US012458810B2

(12) United States Patent
Müller-Bruhn et al.

(10) Patent No.: US 12,458,810 B2
(45) Date of Patent: Nov. 4, 2025

(54) RESPIRATION PROMOTING APPARATUS AND USE THEREOF

(71) Applicant: STIMIT AG, Biel/Bienne (CH)

(72) Inventors: Ronja Müller-Bruhn, Windisch (CH); Peter Frei, Gersau (CH)

(73) Assignee: STIMIT AG, Biel/Bienne (CH)

( * ) Notice: Subject to any disclaimer, the term of this patent is extended or adjusted under 35 U.S.C. 154(b) by 819 days.

(21) Appl. No.: 17/286,734

(22) PCT Filed: Oct. 18, 2019

(86) PCT No.: PCT/EP2019/078451

§ 371 (c)(1),
(2) Date: Apr. 19, 2021

(87) PCT Pub. No.: WO2020/079266

PCT Pub. Date: Apr. 23, 2020

(65) Prior Publication Data

US 2021/0379394 A1 Dec. 9, 2021

(30) Foreign Application Priority Data

Oct. 19, 2018 (EP) .................................... 18201496

(51) Int. Cl.
*A61N 2/00* (2006.01)
*A61N 2/02* (2006.01)

(52) U.S. Cl.
CPC ............... *A61N 2/006* (2013.01); *A61N 2/02* (2013.01)

(58) Field of Classification Search
CPC .................................. A61N 2/006; A61N 2/02
See application file for complete search history.

(56) References Cited

U.S. PATENT DOCUMENTS

2006/0142748 A1 6/2006 Foreman et al.
2016/0310730 A1 10/2016 Martins et al.
(Continued)

FOREIGN PATENT DOCUMENTS

DE 1718255 U 3/1956
DE 3303392 C1 6/1984
(Continued)

OTHER PUBLICATIONS

International Search Report and Written Opinion of the International Searching Authority issued Jan. 17, 2020, in corresponding International Patent Application No. PCT/EP2019/078451.
(Continued)

*Primary Examiner* — Christine H Matthews
(74) *Attorney, Agent, or Firm* — MEDLER FERRO WOODHOUSE & MILLS PLLC

(57) ABSTRACT

A respiration promoting apparatus and a method for promoting respiration for coordinately stimulating two Phrenic nerves of a patient for activating a diaphragm of the patient including a first coil unit and as second coil unit. The first coil unit is configured to be positioned at the patient to stimulate a first Phrenic nerve of the patient. The second coil unit is configured to be positioned at the patient to stimulate a second Phrenic nerve of the patient. The first coil unit has a non-flat first coil winding formed from a conductive elongate component, and the second coil unit also has a non-flat second coil winding formed from a conductive elongate component. A control unit coordinatedly provides current through the first coil winding and the second coil winding such that the first and second Phrenic nerves are stimulated, and a diaphragm of the patient is homogeneously activated.

20 Claims, 8 Drawing Sheets

(56) References Cited

U.S. PATENT DOCUMENTS

| | | | | |
|---|---|---|---|---|
| 2017/0291038 | A1 | 10/2017 | Midorikawa et al. | |
| 2019/0255346 | A1* | 8/2019 | Ghiron | A61N 2/006 |
| 2022/0362570 | A1 | 11/2022 | Pemberton | |

FOREIGN PATENT DOCUMENTS

| | | | |
|---|---|---|---|
| DE | 10 2007 013531 | A1 | 9/2008 |
| EP | 2666515 | A1 | 11/2013 |
| GB | 2261820 | A | 6/1993 |
| GB | 2587392 | A | 3/2021 |
| WO | 2007/121360 | A2 | 10/2007 |
| WO | 2010/109298 | A1 | 9/2010 |
| WO | 2013/012948 | A1 | 1/2013 |
| WO | 2021059250 | A1 | 4/2021 |

OTHER PUBLICATIONS

Communication under Rule 71(3) EPC issued Apr. 8, 2024 in EP Appl. No. 20 789 645.7.

* cited by examiner

RESPIRATION PROMOTING APPARATUS AND USE THEREOF

TECHNICAL FIELD

The present invention relates to an electro-magnetic respiration promoting apparatus for stimulating Phrenic nerves of a human or animal being and a use of the respiration promoting apparatus in a method for promoting respiration of a human or animal. More particularly, the present invention relates to a non-invasive electro-magnetic respiration promoting apparatus using a first coil winding unit for stimulating a first Phrenic nerve and a second coil winding unit for stimulating a second Phrenic nerve.

BACKGROUND ART

In medicine, it is known that for many purposes it is beneficial to activate a target tissue of a patient using stimulation by electro-magnetic fields. For achieving such activation of tissues in a patient's body, it is known to directly stimulate the tissue or to indirectly activate the tissue via stimulation of specific parts of the neural system. For example, the target tissue being a muscular tissue can be activated by providing electric pulses directly to the muscular tissue or to nerves associated to the muscular tissue.

In practice, electro-magnetic stimulators are used to activate a target tissue. Such devices are based on the principle of electro-magnetic induction: a strong current pulse (typically a monophasic or biphasic current pulse) flows through a coil winding, which produces a strong, transient magnetic field. The current pulses cause a changing magnetic field altering according to the phases of the current pulses. The changing magnetic field induces a corresponding electric field, which in turn depolarizes neuronal membranes, leading to action potentials through one or more nerves. Coil windings are usually designed towards generating electric field distribution curves of the induced field, often having an electric field peak (area with maximum electric field strength) or an electric field area, which is stronger than others in other areas. Thus, an electric field distribution curve can generate activation pulses, which are effective periodically at time intervals, and electric field peaks or strong field areas may alternate with low field areas in the distribution curve.

Double coils may have an electric field peak coincident with the area between both coils or overlapping coil areas depending on the current flow direction in both coils, because the electric field components may sum up in these areas.

Double coils, also referred to as butterfly coils, with large radii of their windings are favourable, to generate an electro-magnetic field with a high penetration depth into the body, in order to stimulate nerves inside the body and minimize effects on the overlying muscles or tissues. Nevertheless, for such coils care must be taken to balance between focality and depth of the electro-magnetic field, known as focality-depth trade-off.

Electro-magnetic stimulators using double coil arrangements are for example known for the treatment of brain tissue like the intracerebral nerve, particularly to relieve symptoms of neurological disorders such as post-stroke pain, depressions and Alzheimers's disease. A transcranial magnetic stimulation system is for example described in US 2017/0291038 A1, which comprises a double coil arrangement in a casing for abutting the surface of a scalp and transmitting a predetermined electro-magnetic field to the intracerebral nerve for activation.

Further, in critical care units of hospitals it may be desired to activate the diaphragm of ventilated patients in order to prevent drawbacks of disuse of the diaphragm. It was shown that disuse atrophy of diaphragm muscle fibres occurs already in the first 18-69 hours of mechanical ventilation, and the muscle fibre cross-sections decreased by more than 50% in this time. Thus, it is aimed to activate the diaphragm repeatedly while the patient is given artificial or mechanical respiration such that the functioning of the diaphragm can be upheld, or to activate the diaphragm at least during the weaning period to support effective restoration of independent respiratory function.

It is known that the diaphragm can be activated by stimulating the two Phrenic nerves, e.g., at the neck of the patient. In this context, US 2016/0310730 A1 describes an apparatus for reducing ventilation induced diaphragm disuse in a patient receiving ventilation support from a mechanical ventilator. The apparatus includes an electrode array of first and second types and comprises a plurality of electrodes configured to stimulate a Phrenic nerve of the patient, and at least one controller identifying a type of electrode array from at least two different types and generating a stimulus signal for stimulating a Phrenic nerve of the patient based upon the identity of the electrode type. Such electrode-based stimulation is not very robust to patient movements or relocations, and the possible stimulation depth can be significantly limited by bones or fatty tissue. Furthermore, electrode stimulation is reported to be more painful for the patient than electro-magnetic stimulation.

Moreover, when two target nerves inside the body in a close distance to each other, like the two Phrenic nerves, shall be stimulated simultaneously, the double coil systems in today's stimulators used for electro-magnetic stimulation have significant limitations. Small sizes of double coils, i.e., coils with small radii, need to be used in order to compensate for space constraints, which produce unfavourable co-stimulation effects on overlying body tissues because due to the focality-depth trade-off, overlying body tissues experience relatively high electro-magnetic fields while the electro-magnetic field in depth is inefficient compared to a coil design including large coil windings. De-central coils have been designed for this purpose producing de-centralized fields and have been described for instance in DE 10 2007 013531 A1. However, typically two separate stimulators are necessary, the electromagnetic fields of the two double coils can interfere with each other, and body constraints may not allow positioning those coils in parallel to make use of the de-centralized design. Especially in the neck region, positioning coils longitudinal to the neck to produce a desirable electro-magnetic field direction would force the user to choose significantly smaller coil sizes because the chin and chest constrain space for the coils to be placed. However, small coil sizes are inefficient in depth and less heating resistant, especially when a current is supplied over elongated periods of time.

Therefore, there is a need for a non-invasive respiration promoting apparatus and use thereof and a non-invasive method for promoting respiration of a patient, which allow for efficient stimulation of both Phrenic nerves, overcome space constrains, avoid co-stimulation effects of tissue in the vicinity of the Phrenic nerves, are simple to apply at a patient as well as are convenient and pain-free for the patient.

DISCLOSURE OF THE INVENTION

According to the invention this need is settled by a respiration promoting apparatus and by a method for promoting respiration of a patient as described in embodiments hereof.

In particular, the invention deals with a respiration promoting apparatus to coordinatedly stimulate two Phrenic nerves of a patient for activating a diaphragm of the patient. The respiration promoting apparatus comprises a first coil unit configured to be positioned at the patient to stimulate a first Phrenic nerve of the patient, and a second coil unit configured to be positioned at the patient to stimulate a second Phrenic nerve of the patient. The first and second Phrenic nerve may be referred to as the right and the left Phrenic nerve. According to the invention the first coil unit has a non-flat first coil winding formed from a conductive elongate component, and the second coil unit has a non-flat second coil winding formed from a conductive elongate component. The conductive elongate component is for example a copper or aluminium wire as commonly used for electric coils. However, other electrically conductive materials may be used as well.

Accordingly, each of the first and second coil units can be associated with one of the first and second Phrenic nerves. The first and second coil units may be positioned relative to their respective Phrenic nerve independent from each other. Nevertheless, an electro-magnetic field created by the respiration promoting apparatus of the present invention at each of first and second Phrenic nerve may result from respective electro-magnetic fields of the first and second coil unit, if required.

The respiration promoting apparatus enables the generation of a localized, topical electromagnetic field which may be applied for targeted stimulation of the Phrenic nerves. The respiration promoting apparatus allows for an effective electro-magnetic field in depth while minimizing electro-magnetic field effects on overlying tissues close to the surface, which could potentially cause pain or other discomfort to patients. The herein disclosed apparatus can generate an electro-magnetic field which is advantageously suitable to stimulate the phrenic nerves located at about 2 to 4 centimetres depth inside a patient's neck or about 2-10 centimetres depth inside a patient's chest.

The first and the second coil units together form a coil unit arrangement, which can produce two electro-magnetic field focal areas and which are specifically designed and arranged to stimulate the two Phrenic nerves simultaneously. The coil unit arrangement is designed to maximize a radius of the first and second coil windings. Further, space constraints can be overcome for cases where a placement of two double coils or the use of two individual stimulators becomes unpracticable, as for example in the neck region of a patient. Accordingly, the first and the second coil unit are independently positioned and produce electro-magnetic field components to depolarize the membrane of the two Phrenic nerves.

The term "non-flat" as used herein can relate to any shape, which is not in a two-dimensional plane. That means, the first and the second coil winding are formed by several spiral-like turns or windings of the conductive elongated component, wherein at least some of the turns of the coil winding are not in the same plane and the spiral-like turns together result in a non-flat surface of the coil winding. Thus, the non-flat coil windings are three dimensional or non-planar bodies. The term "non-flat" can for example cover bent shapes or the like.

The three dimensionally shaped or non-flat coil windings can provide field strengths with higher penetration depths than two dimensional coil windings. Moreover, three dimensional coil windings heat up less and provide better cooling possibilities when compared to flat coil windings under the same operating regime. In particular, the three dimensionally shaped coil windings may be provided with a comparatively large cross section while at the same time restricting the surface intended to contact a patient's body (the coil windings of the outwards curved exterior surface in contact to the body will be responsible for the desired effects while the coil windings further away to the body will optimize cooling possibilities).

Preferably, the first coil winding and the second coil winding are convex coil windings. For example, such convex coil winding may result from several spiral-like turns which together form an outwards curved exterior surface of the coil windings. Therefore, the first and the second coil winding preferably have a convex outer side and a concave inner side. Particularly, the first coil winding and the second coil winding may have an essentially conical shape. Like this, the coil windings can be cone coils or cone coil windings. Further, at least one of the convex coil windings may have a cross section in an essentially spherical shape, which means each of the convex coil windings may have a cross section in an essentially spherical shape. Thereby, the spherical shape can form a portion of a circle.

The outwards curved exterior surface of the coils can be positioned on soft body tissue and with slight, physiologically tolerable pressure on the coils (e.g., created by the coil weight itself). Thus, the coil windings on the outwards curved exterior surface that is impressed into the body can get closer to the target nerve. Any distance reduction between coil wire and target nerve will result into higher effectiveness because electro-magnetic fields are reduced exponentially with increasing distance to the source.

Advantageously, both coil windings have the same non-flat shape. Thus, for example each of the coil windings has a cross section in an essentially conical shape.

The first and second coil units according to the present invention are particularly suitable and effective for the stimulation of both Phrenic nerves via placement of the coil units at their respective positions on the neck or on the chest on an area above a phrenic nerve.

Thus, according to a method for promoting respiration of a patient according to the present invention the non-flat first coil winding formed from the conductive elongate component is positioned at the patient such that the first Phrenic nerve of the patient is in an electro-magnetic field generatable by the first coil winding, and the non-flat second coil winding formed from the conductive elongate component is positioned at the patient such that the second Phrenic nerve of the patient is in an electro-magnetic field generatable by the second coil winding. A current is coordinatedly provided through the first coil winding and the second coil winding such that the first and second Phrenic nerves are stimulated and a diaphragm of the patient is homogeneously activated.

The term "homogeneously activated" in connection with the diaphragm may relate to a uniform motion of the diaphragm. In particular, homogeneous activation may prevent that the diaphragm is more active at one portion such as a hemisphere than at another portion.

The first and the second coil unit may provide bilateral stimulations of the phrenic nerves. This is useful for diaphragm activations, particularly for mechanically ventilated patients to avoid diaphragm atrophy and ventilator-related side effects, for patients lacking respiratory stimulus (e.g., paraplegic patients, patients in need for reanimation, sleep apnea patients second degree), for diagnostic purposes to determine diaphragm strength of patients, and for many other applications where it is useful to stimulate the diaphragm.

In one exemplary use, the respiration promoting apparatus may be applied to the patient's neck or chest to generate the localized electro-magnetic field in a localized gap next to the sternocleidomastoid muscle or at a location with minimum overlying muscular structures, where stimulation of overlying muscular structures can be avoided. Thus, the Phrenic nerve at a depth of about 2-4 cm inside a patient's neck can be stimulated by generating a coordinated electro-magnetic field in the first and second coil unit. Advantageously, the electro-magnetic field does not extend field amplitudes over a certain threshold level. Thus, the electro-magnetic field does not extend too far beyond the target area of the Phrenic nerves and therefore does not affect or co-stimulate the larynx and the sternocleidomastoid muscle.

In an embodiment of a respiration promoting apparatus according to the present invention comprising a first and second coil unit with convex coil windings, each of the first coil unit and the second coil unit has a forward face to be directed to a patient in use of the apparatus and a backward face opposite to the forward face. The forward face of the first coil unit is adjacent to a convex side of the first convex coil winding and the backward face of the first coil unit is adjacent to a concave side of the first convex coil winding. Likewise, the forward face of the second coil unit is adjacent to a convex side of the second convex coil winding and the backward face of the second coil unit is adjacent to a concave side of the second convex coil winding. Therefore, the outermost turn of the coil winding with the largest diameter may be located towards the backward face of the coil unit. The innermost turn of the coil winding with the smallest diameter may be located towards the forward face of the coil unit. By having the convex side of the coil windings directed towards the forward faces, it is achieved that in use of the respiration promotion apparatus, the convex sides of the coil windings are directed to the patient. Thus, the forward face directed to the patient, which may serve as a contact surface, can be smaller than having the concave side of the coil windings directed towards the forward face. Like this, a targeted electromagnetic field can be generated and applied to the patient. Thereby, the Phrenic nerve can efficiently be stimulated and stimulation of other tissue around the Phrenic nerve can be reduced or prevented.

In an embodiment of a respiration promoting apparatus according to the present invention each of the first coil winding and the second coil winding may have an oval base shape. The base shape can for example be defined by the outermost turn or winding of the coil windings. Generally, all of the spiral-like turns of the coil winding may have an oval shape similar to the oval base shape. However, due to the non-flat nature of the first and second coil winding, turns with a small radius that are close to the coil winding axis may have a shape differing from the turns with larger radii further away from the coil winding axis. The oval base shape may comprise an elliptic shape at opposing sides of the winding. By providing coil windings with oval base shapes, oval electro-magnetic fields can be generated. Like this, the electro-magnetic fields can be longitudinally stretched such that, under certain circumstances, the electro-magnetic field can be better provided distant from muscular structures towards the Phrenic nerves. For example, the longitudinally extending electro-magnetic fields facilitate the positioning of the coil units near or adjacent to the sternocleidomastoid muscles for stimulating the Phrenic nerves. Like this, side effects in use of the apparatus can be lowered or prevented. An oval base shape may allow for providing a comparably large contact surface by locating a wide curved portion of the oval base shape at the patient such that the coil units can be safely and stably positioned at the patient. Or, the oval base shape may allow to apply a comparably narrow electro-magnetic field to the patient by positioning the narrow curved portion of the oval shape at the patient and/or to impress the coil unit to a comparably large extent into the skin of a patient. In general, by designing the coil windings with the oval base shape, the electro-magnetic field can be geometrically shaped as desired.

Further, in an embodiment of a respiration promoting apparatus according to the present invention the first coil winding can have a first winding direction, the second coil winding can have a second winding direction, and the first winding direction and the second winding direction can be identical. The winding direction can particularly be clockwise or counter-clockwise direction. However, as mentioned the first and second coil windings advantageously have the same orientation, ether both are clockwise, or both are counter-clockwise. In an area in between the first coil unit and the second coil unit, this results in an opposing current direction through the conductive elongate component of the coil windings. Thus, if the coil units are placed side-by-side or in some distance to each other, the generated electro-magnetic fields of the two coil units are in opposite direction in the overlap area. Particularly, at an interface between the two coil units, this results in a cancelling effect of the electro-magnetic fields of the two coil units, whereby the resulting electro-magnetic field is weakened or completely cancelled out depending on the current flow in each of the coil units.

By having identical winding directions in the first and second coil windings it can be prevented that a peak is generated at the overlap area of the electro-magnetic fields generated by the first and second coil windings. Also, the risk that the coil units or coil windings are attracted by each other may be reduced. This allows for providing increased safety for the use of the respiration promoting apparatus.

In an embodiment of a respiration promoting apparatus according to the present invention the first coil unit has a first housing encasing the first coil winding and the second coil unit has a second housing encasing the second coil winding. By such housings the coil windings can be encased and protected. Furthermore, such housings allow for assuring correct positioning of the coil units at the patient. The housings are suitably designed for receiving the coil windings. Advantageously, the housings may comprise a front face and a back face such that the forward face and the backward face of the coil units are arranged next to these faces accordingly. Thus, the front face of the housing can be placed towards a patient to orient the forward face of the coil unit in direction of the patient.

Further, the respiration promoting apparatus preferably may comprise a control unit configured to coordinatedly provide current to the first coil unit and to the second coil unit, respectively. Advantageously, the control unit is configured to simultaneously provide current to the first coil unit and to the second coil unit. Thus, by coordinating each of the current flows in the first and second coil unit the respiration promoting apparatus can coordinatedly stimulate the two Phrenic nerves as required for optimal activation of the diaphragm.

Also, the control unit can comprise a power supply coupled to the first coil winding of the first coil unit and to the second coil winding of the second coil unit, wherein the control unit is configured such that the power supply provides current through the first coil winding in a circulation direction and through the second coil winding in the same circulation direction. The term “circulation direction” can particularly relate to a clockwise or counter-clockwise direction. In such an embodiment, the first and second coil units may be operated in a reverse current mode. Like this, the electromagnetic fields generated by the two coil units can cancel each other in an area between the coil units. Thereby, undesired effects or side effects provided to the patient can be prevented. Also, it can be prevented that the coil units disturb each other in operation.

Additionally, the respiration promoting apparatus according to the invention may comprise a first biofeedback sensor coupled to the control unit and a second biofeedback sensor coupled to the control unit. Preferably, the first biofeedback sensor is associated to the first coil unit and the second biofeedback sensor is associated to the second coil unit. The biofeedback sensors are configured to receive an activation feedback signal upon detection of the activation of the Phrenic nerves and/or the diaphragm. Advantageously, the control unit is configured to individually provide current to the first coil unit and to the second coil unit in accordance with the feedback signals received from the first biofeedback sensor and the second biofeedback sensor such that the diaphragm is uniformly activated.

Particularly, in use for the method for promoting respiration of a patient the first biofeedback sensor is positioned at the patient such that it provides a first feedback signal about contractility of a first diaphragm hemisphere, and the second biofeedback sensor is positioned at the patient such that it provides a second feedback signal about contractility of a second diaphragm hemisphere. In accordance with the first feedback signal and the second feedback signal, the current is coordinatedly provided through the first coil winding and the second coil winding. By involving the first and second biofeedback sensors, the method allows for automatically stimulating the diaphragm of the patient in a homogeneous manner.

Preferably, the biofeedback sensors comprise at least one electrode configured to be attached to the patient such that it senses an activity of the respective Phrenic nerve. Such biofeedback sensors can efficiently detect activation of the nerves such that the electro-magnetic field can be calibrated, and proper functioning of the stimulation can be monitored.

The control unit may comprise an electro-magnetic field adjustment mechanism that is configured to automatically adjust or vary a field strength or amplitude of the electro-magnetic field generated by the coil arrangement of the respiration promoting apparatus. Particularly, when a predefined threshold of the electro-magnetic field is reached, the field can be reduced and adjusted. Also, the electro-magnetic field adjustment mechanism may automatically stop variation of the field strength of the electro-magnetic field when a satisfying activation feedback is received from the biofeedback sensors. Thus, the control unit allows to efficiently adjust and dimension of the electro-magnetic field or its required shape in order to achieve desired depolarization of the membrane of the Phrenic nerves without negative effects on surrounding tissue.

In another embodiment of the respiration promoting apparatus according to the present invention the apparatus comprises a third coil winding formed from a conductive elongate component, which is arranged in an area in between the first coil winding and the second coil winding, wherein the three coil windings together produce two areas of strong magnetic fields. All three coil windings could for example be arranged in the same plane, wherein the plane could be bent for example to follow the curve of a patient’s neck.

Also, the third winding could be slightly offset with respect to the first and second coil winding. That means the third coil winding could be offset with respect to a straight line connecting the first coil winding and the second coil winding. Also, the third coil winding could overlap with the first and second coil winding. The third coil winding can be used to strengthen the electro-magnetic field generated by the first and second coil windings. Preferably, the first and the second coil are located relative to the third coil winding such that the main electro-magnetic field direction is oriented in a direction that will depolarize the phrenic nerves. More preferably, the coil windings are located relative to each other such that the electro-magnetic field is not oriented parallel to the nerve.

Preferably, the first coil winding and the third coil winding are arranged to provide a first electro-magnetic field peak to stimulate the first Phrenic nerve of the patient, and the second coil winding and the third coil winding are arranged to provide a second electro-magnetic field peak to stimulate the second Phrenic nerve of the patient. The first field peak is a result of overlying electro-magnetic fields generated by the first coil winding and the third coil winding and is targeted to depolarize the membrane of the first Phrenic nerve. Likewise, the second field peak is a result of overlying electro-magnetic fields generated by the second and the third coil winding and is targeted to depolarize the membrane of the second Phrenic nerve. The location of the peaks can for example be adjusted by changing the current flow in the coil windings creating the electro-magnetic field peak, or by changing the distance of the coil windings to each other. For example, the location of the electro-magnetic field peaks may be identified using a biofeedback sensor as mentioned above.

In a further embodiment of the respiration promoting apparatus according to the present invention the apparatus comprises further coil windings can be used to customize the electro-magnetic field peaks for stimulating the two Phrenic nerves. For example, a fourth and a fifth coil winding could be arranged next to the first and second coil winding. In this case, the location of the two electro-magnetic field peaks generated by the respiration promoting apparatus can for example be adjusted by overlying a fourth winding with it’s centre above the intersection of the first and the third coil winding and by overlying a fifth coil winding with it’s centre above the intersection of the third and the second coil winding and by changing the current flow in the fourth and fifth coil windings to change position of the electro-magnetic field peak, or by changing the distance of the coil windings to each other.

The third coil winding and any additional coil windings, respectively, can contribute to the stimulation of the first Phrenic nerve and the second Phrenic nerve and as such the third coil winding and any additional coil windings can be considered being part of the first coil unit as well as the second coil unit of the respiration promoting apparatus. However, the third coil winding may be received in a third housing separate to the first and second housing of the first and second coil units, and any additional coil windings may be received in additional housings. Alternatively, all coil units may be arranged in a common housing.

Further, although the third coil winding may assist in sharpening and targeting an electro-magnetic field provided by the first coil unit and the second coil unit, there might be physiological instances where the electro-magnetic field of the third coil winding or any additional coil winding is not required to provide optimal stimulation of a Phrenic nerve and therefore the third coil winding may not be in use in such a case.

Preferably, at least the third coil winding has an essentially bent or kinked shape. That means the turns or the windings of the third coil winding are arranged in a plane, which is bent or kinked with respect to an axis essentially perpendicular to the coil winding axis. However, a bending radius may vary in the bent shape of the coil winding. In a kinked shape there may be one kink resulting in a V-shape of the coil winding, or there may be more than one kink resulting in a bend-like shape. Due to the bent or kinked shape of the third coil winding in between the first and second coil winding, the overall coil arrangement comprising all three coil windings essentially arranged in line or in a curved line also is in a bent or kinked shape. In case there are more than three coil windings in the coil arrangement, the overall arrangement can be in a bend or kinked line or plane. Thus, the coil arrangement of the respiration promoting apparatus basically is designed in a two-dimensional array.

This helps to position the desired field peak being a result of overlying electro-magnetic fields (i.e., the areas beneath the first and third coil winding intersection and the area beneath the second and third coil winding intersection) with minimum distance to the neck while positioning the irrelevant coil areas further away from the neck. Advantageously the first coil winding and the second coil winding comprise an oval base shape to elongate the shape of the peak area.

However, it is emphasised that the third coil winding can advantageously contribute to shape the electro-magnetic fields of the first and the second coil units independent of the shape of the first and the second coil windings. That means, the first and the second coil winding could be realized as flat coil windings. Therefore, it is a further aspect of the present invention to provide a respiration promoting apparatus to coordinatedly stimulate two Phrenic nerves of a patient for activating a diaphragm of the patient, which comprises a first coil unit having a first coil winding formed from a conductive elongate component and being configured to be positioned at the patient to stimulate a first Phrenic nerve of the patient, a second coil unit having a second coil winding formed from a conductive elongate component and being configured to be positioned at the patient to stimulate a second Phrenic nerve of the patient, and a third coil winding formed from a conductive elongate component, which is arranged in an area in between the first coil winding and the second coil winding.

Such an apparatus allows for efficient stimulation of both Phrenic nerves by generating and optimizing the shape of the electro-magnetic field peaks provided by the first and the second coil units. Further, the apparatus overcomes space constrains by providing flexible positioning of the coil units generating the stimulating electro-magnetic fields. The resulting electro-magnetic field peaks can avoid co-stimulation effects on tissue surrounding the Phrenic nerves. Also, the apparatus is simple to apply around a patient's neck and it is convenient and pain-free for the patient.

The respiration promoting apparatus comprising the coil arrangements and supporting structures described herein are typically provided with biphasic or monophasic currents in the wires. Current directions are typically reversible. The alternating currents induce alternating magnetic fields, which in turn induce alternating electric field components. Those are used to depolarize nerve membranes. An electric field component vertical to the membrane will depolarize the membrane. In embodiments where two adjacent coil units are operated with currents having opposing rotational directions the main electric field component is typically created at the centre between the two adjacent coil windings, in a direction vertical to a virtual axis connecting centres of the two coil windings. Therefore, it is desirable to place this virtual axis parallel to the nerve.

In use of the respiration promoting apparatus for activating the Phrenic nerves, the respiration promoting apparatus generates two peaks in the body areas between the coil windings, wherein advantageously the main electric field peaks are induced above the two Phrenic nerves, and the main electric field component direction is angled more than 200 and less than 1600 relative to the Phrenic nerves, in order to induce a potential difference along the nerve membranes.

BRIEF DESCRIPTION OF THE DRAWINGS

The respiration promoting apparatus and the method for promoting respiration of a patient according to the invention are described in more detail herein below by way of exemplary embodiments and with reference to the attached drawings, in which.

DESCRIPTION OF EMBODIMENTS

FIGS. 1 to 4 show different embodiments of respiration promoting apparatuses according to the present invention, which comprise a bracket structure coupled to coil units for positioning the apparatus at a patient and coordinatedly stimulating two Phrenic nerves. FIGS. 5 to 11 schematically show the concepts and applications of a respiration promoting apparatus of the invention for coordinatedly stimulating the two Phrenic nerves. Further, a method of promoting respiration of a patient according to the present invention may use any of the respiration promoting apparatus and concepts disclosed in FIGS. 1 to 11. Particularities of the method will be described in context of the illustrated example embodiments. The concepts and applications illustrated in FIGS. 5 to 11 may make use of a bracket structure as illustrated in FIGS. 1 to 4 but also may use other positioning arrangements for positioning coil units of the apparatus as commonly known.

In the following description certain terms are used for reasons of convenience and are not intended to limit the invention. The terms “right”, “left”, “forward”, “backward”, etc. refer to positions relative to a patient unless otherwise indicated the description. The terminology comprises the explicitly mentioned terms as well as their derivations and terms with a similar meaning. Also, spatially relative terms, such as “beneath”, “below”, “larger”, “above”, “upper”, “smaller”, “proximal”, “distal”, and the like, may be used to describe one element’s or feature’s relationship to another element or feature as illustrated in the figures or indicated in the description.

To avoid repetition in the figures and the descriptions of the various aspects and illustrative embodiments, it should be understood that many features are common to many aspects and embodiments. Omission of an aspect from a description or figure does not imply that the aspect is missing in embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part or component are provided with reference signs it is referred to other drawings showing the same part or component. Like numbers in two or more figures represent the same or similar elements or elements with the same functionality.

Figure 1A:
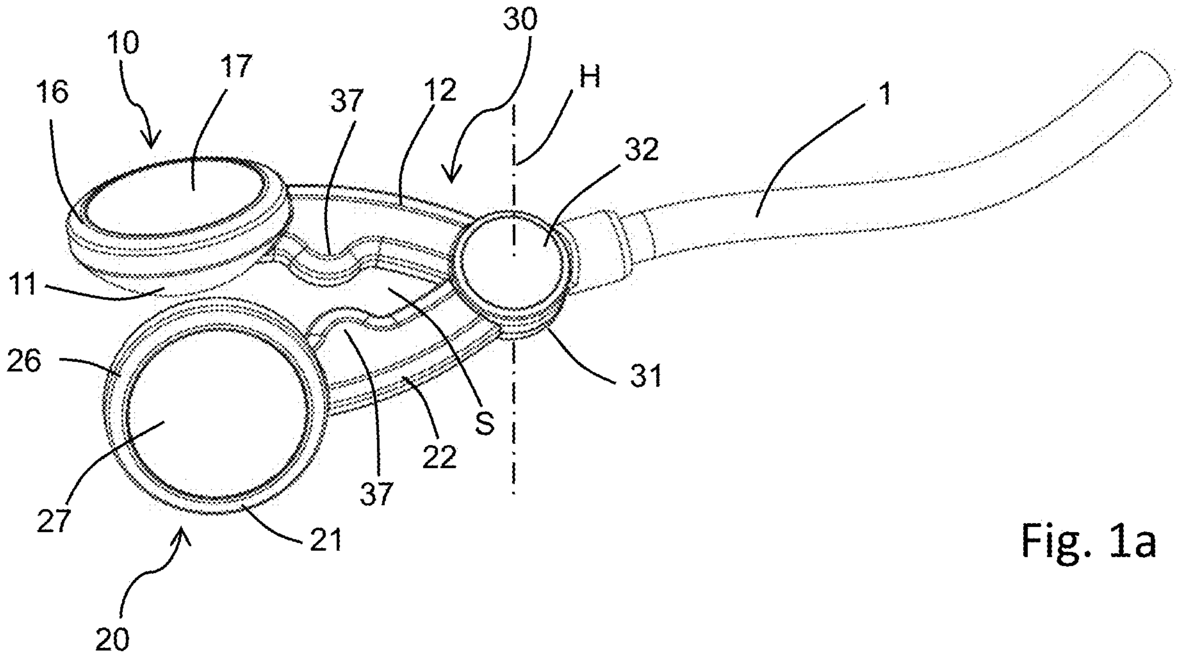
FIG. 1*a* shows a first embodiment of a respiration promoting apparatus according to the present invention comprising a first coil unit, a second coil unit and a bracket structure in a narrow configuration.
Figure 1B:
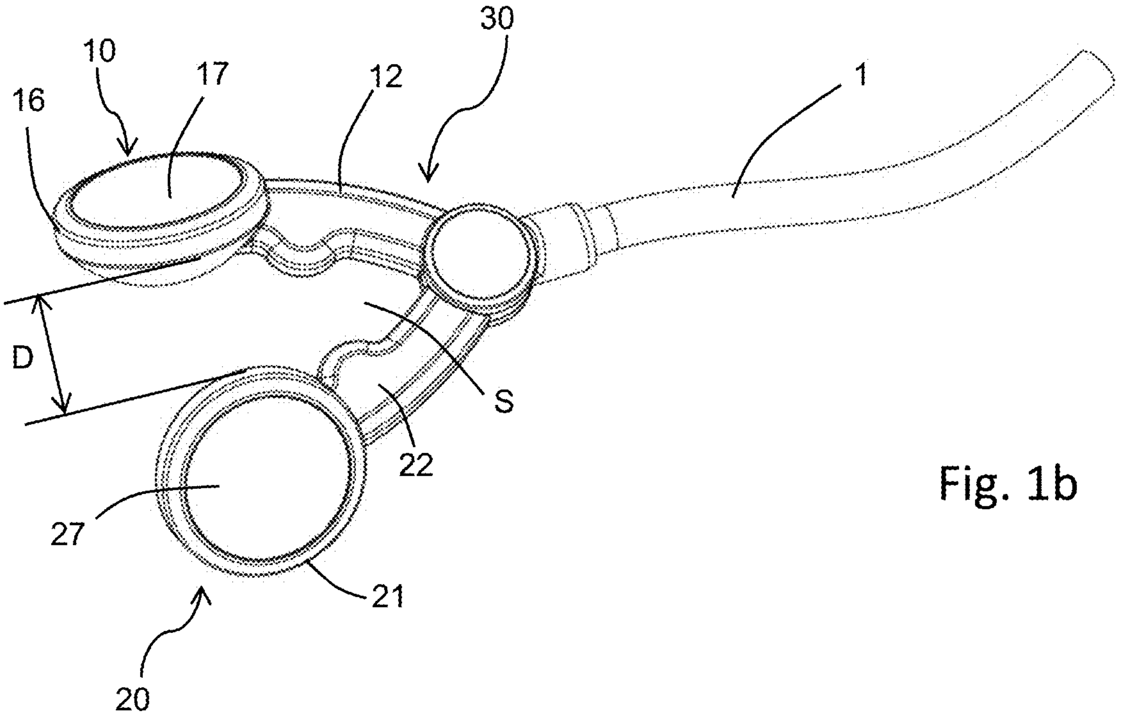
FIG. 1*b* shows the first embodiment of a respiration promoting apparatus in a wide configuration.

FIGS. 1*a* and 1*b* illustrate a first embodiment of a respiration promoting apparatus to coordinately stimulate two Phrenic nerves (not shown) of a patient for activating a diaphragm of the patient. The respiration promoting apparatus comprises a first coil unit 10 having a first forward face 11 configured to be positioned at the patient to stimulate a first Phrenic nerve of the patient and a second coil unit 20 having a second forward face 21 configured to be positioned at the patient to stimulate a second Phrenic nerve of the patient. The respiration promoting apparatus further comprises a bracket structure 30 coupled to the first coil unit 10 and the second coil unit 20. Advantageously, the coil units 10, 20 can be detachably couples to the bracket structure 30. In this case, the bracket structure 30 can easily be replaced in case needed.

Each of the coil units 10, 20 comprises a housing 16, 26 for accommodating the associated coil winding 13, 23 and providing contact surfaces to be positioned at the patient. The first coil unit 10 has a first housing 16 encasing a non-flat first coil winding 13 and the second coil unit 20 has a second housing 26 encasing a non-flat second coil winding 23. By such housings 16, 26 the coil windings 13, 23 of the coil units 10, 20 can be encased and protected. Also, the housing 16, 26 with the coil winding 13, 23 safely positioned and precisely oriented therein allows for assuring correct positioning and orienting of the coil winding 13, 23 relative to the patient and relative to each other. Further, the housings 16, 26 can provide suitable surfaces for the forward faces of the coil units, for example to be positioned at the patient. Thus, a surface of the first housing 16 serves as the first forward face 11 of the first coil unit 10 and a surface of the second housing 26 serves as the second forward face 21 of the first coil unit 20.

The bracket structure 30 is releasably connected to a current supply cable 1 for coordinatedly providing current to the first and the second coil units 10, 20 for generating electro-magnetic fields such that the first Phrenic nerve 62 and the second Phrenic nerve 62 of the patient are stimulated and a diaphragm of the patient is homogeneously activated. Each of the first and the second coil units 10, 20 comprises the non-flat coil winding 13, 23 formed from a conductive elongate component as described above with respect to FIGS. 5 to 8 for generating the electro-magnetic fields suitable for stimulating the two Phrenic nerves 62 for activating the diaphragm of the patient. For example, the elongate component can be a metal wire such as a copper wire or the like.

The coil windings 13, 23 can be positioned and fixed within the housings 16, 26 of the coil units 10, 20 such that a side of the coil winding 13, 23 that is determined to face towards the patient is oriented towards the housing surface providing the forward face 11, 21 of the respective coil unit 10, 20. In case of non-flat coil windings, as for example convex coil windings as further described below, the housing may have a similar three-dimensional shape as the coil windings. Thus, the orientation of the non-flat coil windings 13, 23 towards a patient can be visually monitored in a simple manner. The housings 16, 26 shown in FIGS. 1 to 4 have a flat surface representing backward faces 17, 27 of the coil units 10, 20, and a bulged surface representing the forward faces 11, 21. Further, circumferential sides of the housing 16, 26 connect the backward facing surface and the forward-facing surface.

The bracket structure 30 is adjusted such that positions and orientations of the first coil unit 10 and of the second coil unit 20 are adapted to the specific needs of a patient and for generating an electro-magnetic field targeted for stimulating the Phrenic nerves of the patient. The bracket structure 30 has a third forward face 31 configured to be positioned at the body of the patient. The respiration promoting apparatus is configured to be arranged at a defined location of the patient when the first forward face 11, the second forward face 21 and the third forward face 31 are positioned at the patient in a chosen configuration of the bracket structure 30 suitable for the specifics of the treatment of the patient. Thus, the positioning and adjustment of the three forward faces 11, 21, 31 define a target configuration of the respiration promoting apparatus.

In use the respiration promoting apparatus is arranged at a defined location of the patient such that the first forward face 11, the second forward face 21 and a third forward face 31 are in contact with the patient. When being positioned at the body, the three forward faces serve as three support points and determine defined contact points on the body. Like this, the respiration promoting apparatus can be stably and precisely positioned with respect to the patient's Phrenic nerves, and at the same time provides access to important areas of the patient's neck. For example, tracheotomy may conveniently be possible while stimulating the Phrenic nerves. The electro-magnetic field generated by the first and the second coil units 10, 20 can be precisely targeted to their respective target Phrenic nerve 62 without implying co-stimulation of other body tissue.

In the embodiment shown in FIGS. 1*a* and 1*b*, the bracket structure 30 comprises a first leg portion 12, a second leg portion 22 and a hinge portion 32 connecting the first leg portion 12 and the second leg portion 23 with each other. In this embodiment the first leg portion 12 and the second leg portion 22 are realized as flat rod elements having a curved shape. The first coil unit 10 is releasably coupled to one end of the first leg portion 12 and the second coil unit 20 is releasably coupled to one end of the second leg portion 22. The hinge portion 32 is arranged at an opposing end of the first and second leg portions 12, 22 and flexibly couples the first and second leg portions 12, 22 at their opposing ends.

Figure 4:
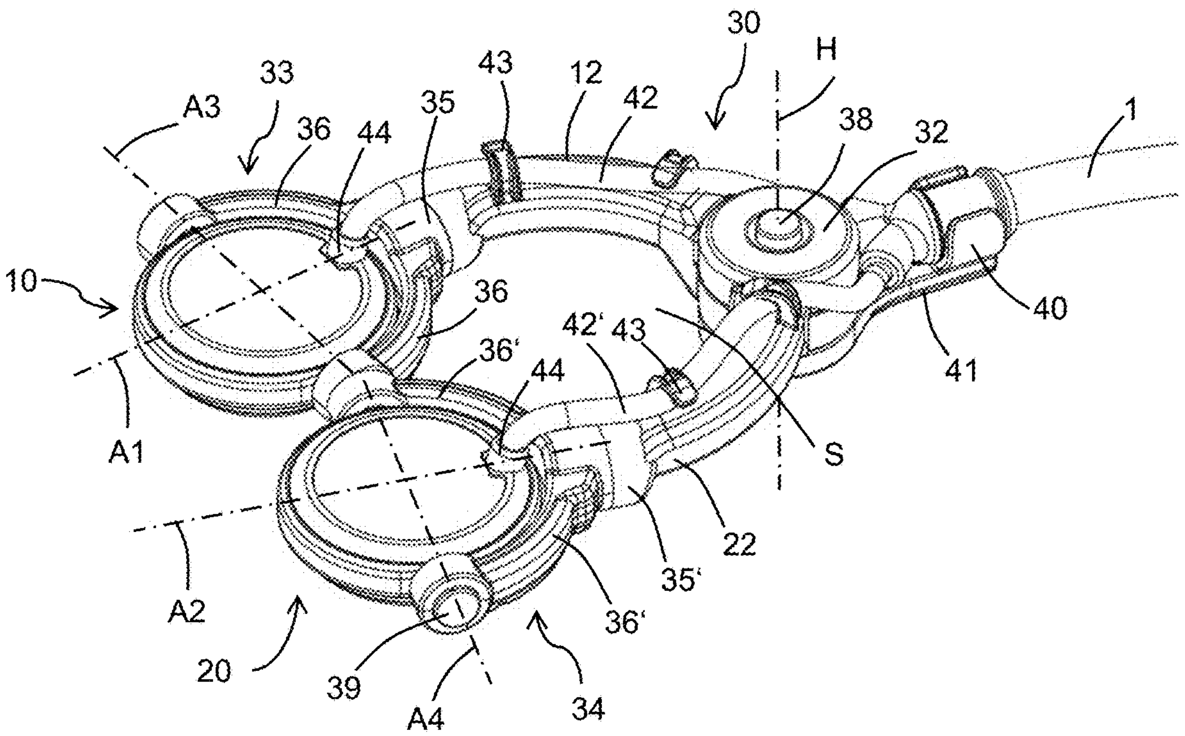
FIG. 4 shows a fourth embodiment of a respiration promoting apparatus according to the present invention comprising a first coil unit, a second coil unit and a bracket structure with pivoting couplers for mounting the coil units.

Further, the rod elements serving as the first and second leg portions 12, 22 each comprise a bulge 39 that extends from a middle section of the rod elements. The bulges 39 may serve for manually handling and adjusting the bracket structure 30. Also, the rod elements may each comprise a fixation arrangement for releasably holding a current line that runs along the leg portion and connects the current supply cable 1 at one end of the leg portions to the coil units 10, 20 at the other end of the leg portions 12, 22. An example for a fixation arrangement is shown in FIG. 4.

In the embodiment of FIGS. 1*a* and 1*b*, the hinge portion 32 is configured as a pivot bearing such that the first and second leg portions can be pivoted around a common articulation axis H of the bearing that runs through the centre of the hinge portion 32. Thus, the leg portions 12, 22 can be swivelled around the axis H in a common two-dimensional plane. Alternatively, the hinge portion 32 could provide more than one articulation axis for adjusting the leg portions three-dimensionally. In this case, the hinge portion 32 could for example be configured as a ball bearing.

The hinge portion 32 allows for adjusting a distance D between the first coil unit 10 and the second coil unit 20 to adapt the position and orientation of the first and second coil units 10, 20 according to a desired target configuration of the bracket structure 30 depending on the requirements for use of the respiration promoting apparatus. FIG. 1*a* shows the respiration promoting apparatus in a narrow configuration of the bracket structure 30 wherein the first coil unit 10 and the second coil unit 20 are in a short distance D from each other. FIG. 1*b* shows the respiration promoting apparatus in a wide configuration of the bracket structure with a larger distance D between the first coil unit 10 and the second coil unit 20.

The curved shape of the first leg portion 12 and the second leg portion 22 guaranties that in any pivoting position of the first leg portion 12 and the second leg portion 22 relative to each other a free space S is provided between the hinge portion 32 and the first leg portion 12 and the second leg portion 22. However, the free space S of the narrow configuration of the bracket structure provides a smaller free area between the leg portions 12, 22 than the wide configuration. In any case, the free space provides ample access to a front area of the neck of a patient that is commonly important for treatment of the patient such as a tracheotomy. The leg portions 12, 22 shown in FIGS. 1*a* and 1*b* are curved in one geometrical plane. However, additionally they could be curved in a second geometrical plane, for example perpendicular to the one plane. Thus, they could create an arch providing additional free space and access to the patient for example from the sides of the neck.

Advantageously, the respiration promoting apparatus rests on the body surface of the patient only with the three forward surfaces 11, 21, 31 located at the first coil unit 10, the second coil unit 20 and at the bracket structure 30. Thus, the three forward surfaces 11, 21, 31 provide support points in a triangular geometry. This enables stable and well-defined positioning at the patient independent of an individual surface landscape of the patient's body while space constrains can be overcome and the respiration promoting apparatus can be carried by the patient conveniently and pain-free. Further, the geometry of the bracket structure determines a target configuration of the respiration promoting apparatus and determines a defined location and orientation of the coil units generating the electro-magnetic fields for activating the diaphragm. This results in efficient stimulation of both Phrenic nerves and avoids co-stimulation effects of tissue in the vicinity of the two Phrenic nerves, particularly in between the two Phrenic nerves where the field could interfere with other medical treatment.

Figure 2:
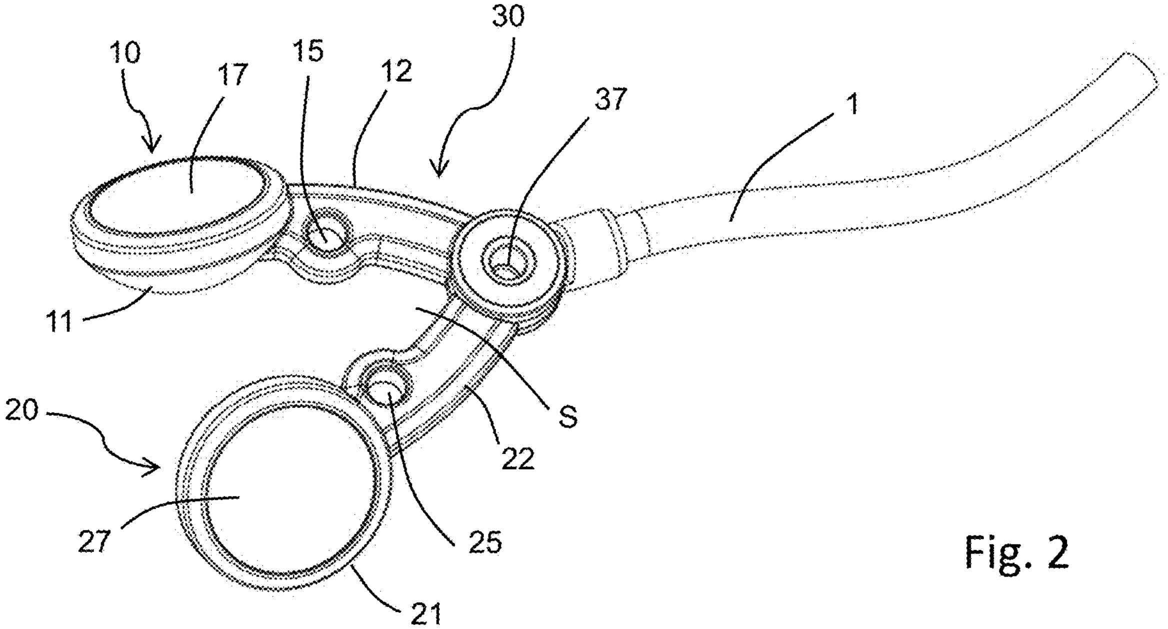
FIG. 2 shows a second embodiment of a respiration promoting apparatus according to the present invention comprising a reference structure.
Figure 3:
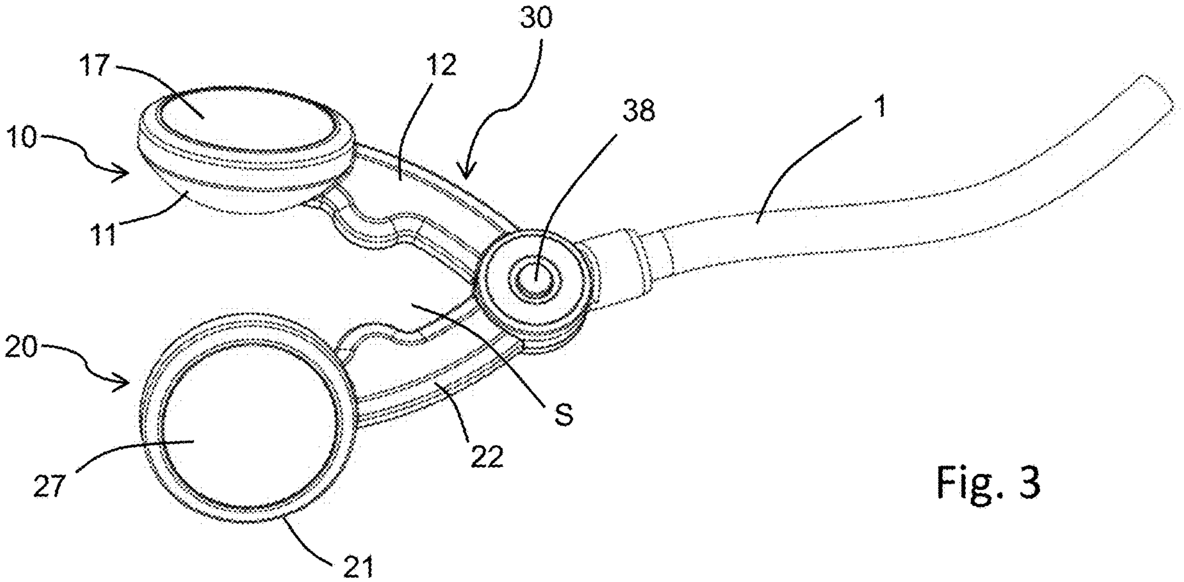
FIG. 3 shows a third embodiment of a respiration promoting apparatus according to the present invention comprising a locking mechanism.

The embodiments of the respiration promoting apparatus according to the invention as shown in FIGS. 2 to 4 are generally configured analogue the embodiment of FIG. 1 but include additional or alternative features to amend the use of the respiration promoting apparatus as described in the following.

In a second embodiment illustrated in FIG. 2, the bracket structure 30 comprises a through-hole 15 in the first leg portion 12, a through-hole 25 in the second leg portion 22 and a through-hole 37 in the hinge portion 32. The through-holes 15, 25, 37 may serve as a reference structure configured to repeatedly locate the respiration promoting apparatus at the defined location of the patient's body. The through-holes 15, 25, 37 allow to align the bracket structure with a specific portion of the body such as at a landmark thereof. By having the reference structure and for example using the natural landmarks of the body, the respiration promoting apparatus can conveniently be re-positioned at the body such that it can be assured that the first and second coil units 10, 20 are properly positioned and oriented to stimulate the first and second Phrenic nerves.

Further, the through-holes 15, 25, 37 can be designed to provide markers to the patient's body there through, when the respiration promoting apparatus is in a desired target configuration. The markers can, for example, be provided by a pen or similar item applying a visual sign on the patient's body. Thus, the markers on the patient's body assist to properly position and orient the first and second coil units 10, 20.

The natural body landmarks and/or the markers also may assist in re-adjusting a bracket structure 30 to an already known suitable configuration. The position and orientation of the coil units 10, 20 can be re-adapted by moving the leg portions 12, 22 to align the landmarks and/or markers with the through-holes 15, 25, 37. Thus, in use of the respiration promoting apparatus the bracket structure can easily be exchanged.

In a third embodiment illustrated in FIG. 3, the bracket structure 30 of the respiration promoting apparatus according to the present invention comprises a locking mechanism to block the position and orientation of the first coil unit 10 and the second coil unit 20 relative to each other in the target configuration of the bracket structure 30. The locking mechanism can for example be provided by a mechanical mechanism or an electrical arrangement. In the present embodiment, the locking mechanism is realized by a locking button 38, which blocks rotation of the first leg portion 12 and the second leg portion 22 in the hinge portion 32 of the bracket structure 30. The locking button 38 can block the movement of the leg portions 12, 22 for example by providing a form fit within the hinge portion 32 in a pushed in or turned position. Alternatively, or additionally, the locking button 38 could block the leg portions 12, 22 by frictional locking. The locking mechanism can prevent changes of the configuration of the bracket structure 30 after the target configuration has been adjusted, which guarantees adequate stimulation of the Phrenic nerves by the respiration promoting apparatus. Thus, the respiration promoting apparatus can be removed from the patient and replaced at a later point in time without the need of recalibration of the coil units 10, 20.

The locking mechanism of the bracket structure 30 can be configured to irreversibly block the position and orientation of the first coil unit 10 and the second coil unit 20 relative to each other in the target configuration of the bracket structure 30. By irreversibly blocking the bracket structure the target configuration cannot accidentally be changed whereby a new adjustment of the respiration promoting apparatus would become necessary.

In a fourth embodiment of the respiration promoting apparatus according to the invention shown in FIG. 4, the coil units 10, 20 are coupled to the bracket structure 30 using U-like shaped pivoting couplers, which are detachably mounted to the bracket structure 30. The U-shape is realized by a stem portion 35 and two symmetrically curved branch portions 36 of the pivoting couplers. As shown in FIG. 4, a first pivoting coupler 33 has a stem portion 35 and two branch portions 36, and a second pivoting coupler 34 has a stem portion 35' and two branch portions 36'. The stem portion 35 of the first pivoting coupler 33 is mounted to an end of the first leg portion 12 and the stem portion 35' of the second pivoting coupler 34 is mounted to an end of the second leg portion 22. The pivoting couplers 33 and 34 basically are arranged in extension of the leg portions at an end thereof. The first coil unit 10 is mounted between the two branch portions 36 of the first pivoting coupler 33 and the second coil unit 20 is mounted between the two branch portions 36' of the second pivoting coupler 34.

The current supply cable 1 is releasably held in a clip mounting 40 arranged at an extension plate 41 extending from the hinge portion 32. The supply cable 1 feeds two current lines 42, 42', which run along the bracket structure 30 and provide current pulses to the first coil unit 10 and the second coil unit 20. The current lines 42, 42' are detachably fixed to the leg portions by fixation fingers 43. The current lines 42, 42' are connected to the coil units by common connectors 44. The supply cable 1 and the current lines 42, 42' can be detached from the bracket structure 30 and from the coil units 10, 20. Thus, they can be used with a different bracket structure and different coil units and the respiration promoting apparatus can easily be modified for different use situations. For example, the bracket structures can be embodied as disposables associated to a specific patient and to be replaced after treatment of the specific patient.

The first pivoting coupler 33 is pivotably mounted to the first leg portion 12 such that the first pivoting coupler 33 can be pivoted relative to the first leg portion 12 about an axis A1 of the first leg portion 12. Respectively, the second pivoting coupler 34 is pivotably mounted to the second leg portion 22 such that the second pivoting coupler 34 can be pivoted relative to the second leg portion 22 about an axis A2 of the second leg portion 22. The leg portion axes A1, A2 are basically aligned with the longitudinal direction of the end portions of the curved leg portion elements and the longitudinal axis of the stem portion 35 of the pivoting couplers. Thus, depending on an adjustment angle of the first leg portion 12 and the second leg portion 22 relative to each other at the hinge portion the leg portion axis A1 and the leg portion axis A2 can enclose different angles. However, pivoting the first coil unit 10 around axis A1 and pivoting the second coil unit 20 around axis A2 can cause the coil units 10, 20 to face more towards or more away from each other in most hinge portion adjustment angles. This can for example result in an increase or decrease of an overlap of the electro-magnetic fields generated by the coil units 10, 20, respectively, and facilitate the alignment of the electro-magnetic fields with the position of the Phrenic nerves.

The first and second coil units 10, 20 are also pivotably mounted between the branch portions 36 such that the first coil unit 10 can be pivoted relative to the first pivoting coupler 33 about an axis A3 and the second coil unit 20 can be pivoted relative to the second pivoting coupler 34 about an axis A4. The axes A3 and A4 basically connect the ends of the branch portions 36, 36' of the respective pivoting coupler.

In summary, the axes A1, A2 along the longitudinal axis of the stem portion 35 define first articulation axes of the pivoting couplers, and the axes A3, A4 crossing the ends of the branch portions 36, 36' within each pivoting coupler define second articulation axes of the pivoting couplers. The first and second articulation axes are essentially perpendicular to each other. Therefore, the coil units 10, 20 can be adjusted in any three-dimensional direction and accordingly an electro-magnetic field generated by the coil units 10, 20 can be provided in any direction required for an optimized stimulation field targeting both of the Phrenic nerves. The angle adjustment of the first and the second coil units 10, 20 for optimized orientation of the coil units 10, 20 can be performed individually according to specific needs of the patient and for generating the targeted electro-magnetic field for stimulating the Phrenic nerves of the patient. Thus, negative side effects during the treatment can be avoided and contact points convenient for the patient can be found.

Preferably, the first and the second coil units 10, 20 are positioned relative to each other such that the electro-magnetic fields of the two coil units 10, 20 only may overlap in their forward direction to create a targeted field for stimulating the Phrenic nerves 62, which helps to control the overall electro-magnetic field provided by the respiration promoting apparatus.

FIGS. 5 to 8 illustrate the concept of a respiration promoting apparatus to coordinatedly stimulate two Phrenic nerves of a patient for activating a diaphragm of the patient according to the present invention. The respiration promoting apparatus comprises a first coil unit 10 configured to be positioned at the patient to stimulate a first Phrenic nerve of the patient, and a second coil unit 20 configured to be positioned at the patient to stimulate a second Phrenic nerve of the patient. Generally, the respiration promoting apparatus can be designed for example like any of the embodiments of a respiration promoting apparatus shown in FIGS. 1 to 4. Therefore, like reference numbers in the figures represent the same or similar elements, or elements with same or similar functionality.

Figure 6:
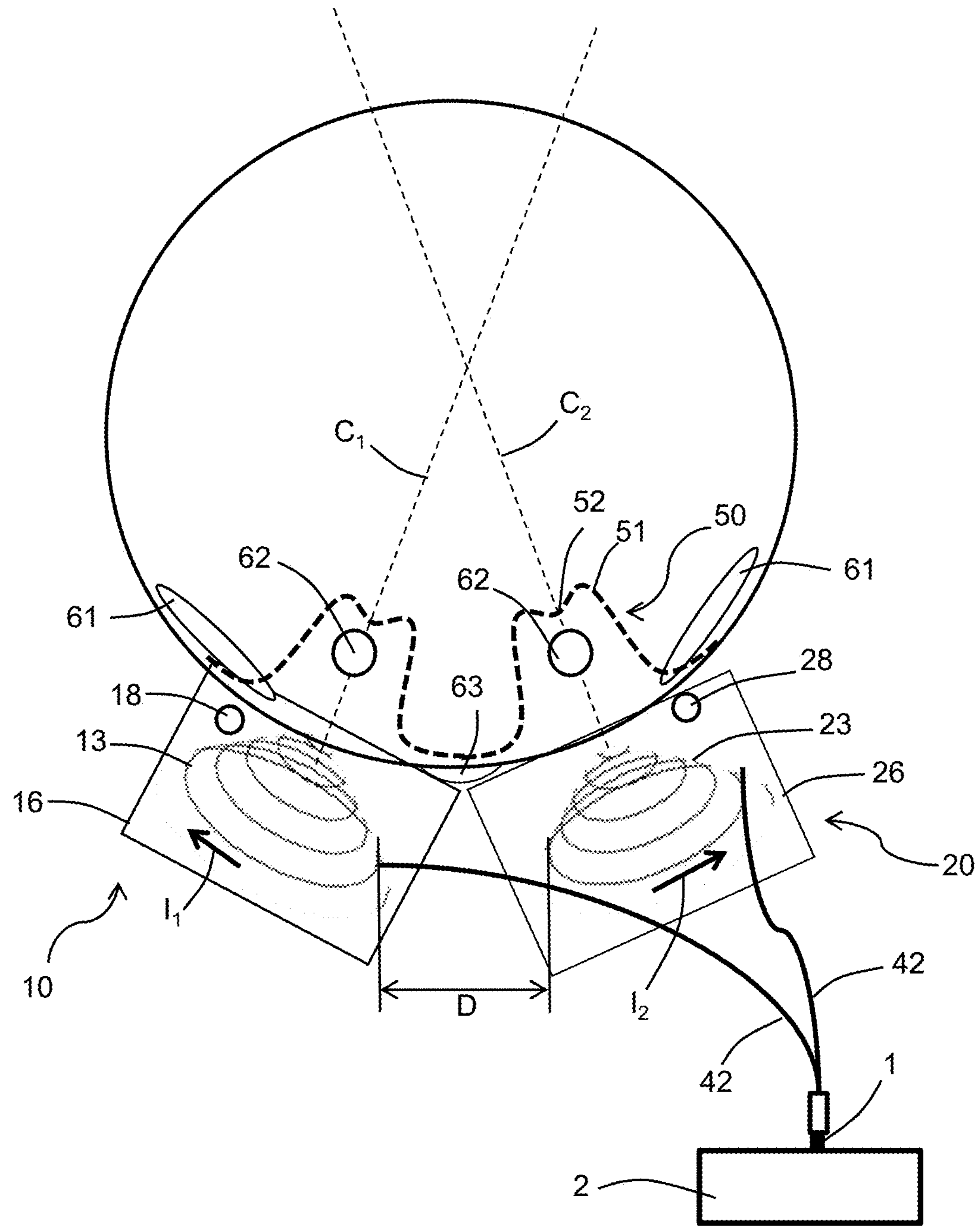
FIG. 6 shows a schematic view of the use of a respiration promoting apparatus according to the present invention comprising a convex first coil winding and a convex second coil winding.

The first coil unit 10 has a non-flat first coil winding 13 formed from a conductive elongate component and the second coil unit 20 has a non-flat second coil winding 23 also formed from a conductive elongate component, as shown in FIG. 6. Each of the two coil windings is formed by a plurality of spiral-like or helically wound turns of the conductive elongate component around a winding axis C of the coil winding. Successive turns decrease in radius starting from an outer turn towards an inner turn close to the winding axis.

Furthermore, at least some of the turns are offset along the winding axis to realize a non-flat shape of the first and second coil winding. Therefore, the first and the second coil windings 13 and 23 are designed as three-dimensional bodies. FIGS. 6, 7*a*, 7*b* and 12*b* show examples, wherein the coil windings have a convex shape, particularly an essentially conical shape.

The convex shape is for example characterized by a bulbous outline of the coil winding 13, 23 resulting from successively elevating adjacent turns starting from an outer turn towards an inner turn such that the inner turns are most elevated relative to the outer turns. Thus, the convex coil windings could for example also have an essentially spherical shape or even an edged or stepped shape. However, the three-dimensional shape of the non-flat coil windings also could have other outlines, for example an undulating shape. The length of the coil winding along its winding axis may be much smaller than the radius of the coil winding turns but still realize a non-flat coil winding.

The three-dimensional nature of the coil windings 13, 23 allows for more flexibility in shaping the electro-magnetic fields generated by the coil windings compared to flat coil winding. In particular, a specifically suitable peak can be created in each electro-magnetic field. Also, for example, the position of electric field peaks or an electric field area with intensified field strength can vary according to the three-dimensional shape of the coil windings. Further, overlapping field areas of the two electro-magnetic fields of the first and the second coil winding can be shaped according to specific needs of the respiration promoting apparatus. A convex shaped coil winding, as for example illustrated in FIG. 6, generates an electro-magnetic field 50 with an exemplified field strength distribution comprising a peaks ring 51 and an inner area 52 inside the peak ring, wherein the peak ring has a maximum field strength and the inner area has only a slightly less field strength. The convex shape of the coil winding facilitates coordination of the field intensity of a peak ring 51 and the inner area 52 inside the peak ring 51, wherein for example different convex shapes can produce different field strength differences. Accordingly, by choosing a specific three-dimensional shape for the coil windings of the coil units the electro-magnetic field created by the respiration promoting apparatus for stimulating the Phrenic nerves can be optimized.

As described before, the non-flat coil windings 13, 23 can be accommodated in housings 16, 26 of the coil units 10, 20. In case of concave coil windings, an outermost turn of the coil winding 13, 23 having the largest diameter is located towards the backward face 17, 27 of the housing 16, 26. The innermost turn of the coil winding 13, 23 having the smallest diameter is located towards the forward face 11, 21 of the housing 16, 26. Thus, the coil windings 13, 23 are positioned in the housings 16, 26 with their base side facing the backward facing surface of the housing 16, 26. Correspondingly, their convex outward facing side is directed towards the forward facing surface of the housing 16, 26. Thus, the base side of the coil windings 13, 23 corresponds to the backward faces 17, 27 of the coil units 10, 20 and the outer side of the convex area of the coil windings 13, 23 corresponds to the forward faces 11, 12 of the coil units 10, 20. By having the convex side of the coil windings 13, 23 directed towards the forward faces 11, 21, it is achieved that in use of the respiration promoting apparatus, the convex sides of the coil windings 13, 23 are directed to the patient. Therefore, such housings 16, 26 guarantee precise positioning of the coil units 10, 20 with the coil winding 13, 23 at the patient.

Figure 5:
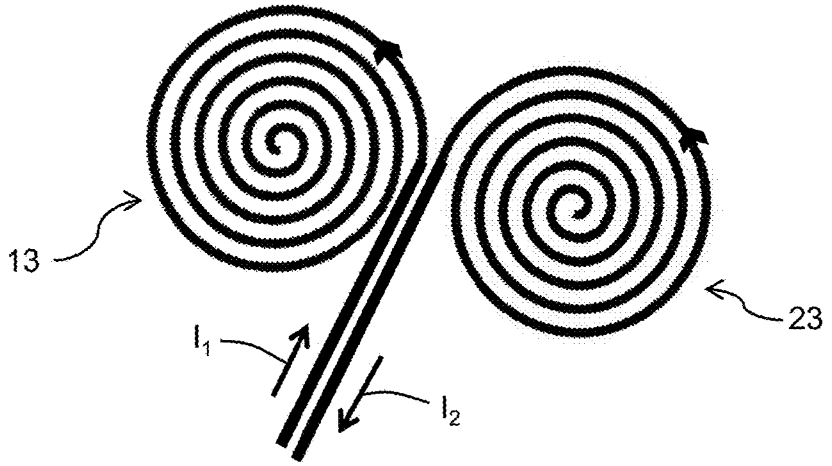
FIG. 5 shows a schematic view of an arrangement of a first coil winding and a second coil winding of a respiration promoting apparatus according to the present invention.

In FIG. 5 the first non-flat coil winding 13 of the coil unit 10 and the second non-flat coil winding 23 of the coil unit 20 are shown in close vicinity to illustrate their respective winding direction and current flow direction. However, as described before when using the respiration promoting apparatus the first coil unit 10 and the second coil unit 20 preferably are arranged in a distance D from each other. In the example shown in FIG. 5 the winding direction of the first coil winding 13 is anti-clockwise and the winding direction of the second coil winding 23 is clockwise. A power supply 2 supplies a current $I_1$ to the first coil winding 13 and a current $I_2$ to the second coil winding 23, for example via a current supply cable 1 and current lines 42 as shown before. The currents $I_1$ and $I_2$ are supplied such that the current flows of the currents $I_1$ and $I_2$ run in opposing direction through the first and second coil windings 13, 23. Therefore, in an area between the coil unit 10 and the coil unit 20 the electro-magnetic fields resulting from the first coil winding 13 and the second coil winding 23 weaken or even cancel out each other. In an alternative example, the winding direction of the first coil winding 13 and the winding direction of the second coil winding 23 can be identical.

FIG. 6 shows a schematic view of a respiration promoting apparatus according to the present invention in use at a neck 60 of a patient seen from the top of the neck. In favour of a better comprehensibility, some of the components of the respiration promoting apparatus are not illustrated in the figures. As mentioned before, the first coil unit 10 and the second coil unit 20 each comprise a conical coil winding 13 and 23. The first coil unit with the first coil winding 13 is placed at an anterior border of a right sternocleidomastoid muscle 61, and the second coil unit with the second coil winding 23 is placed at an anterior border of a left sternocleidomastoid muscle 61, wherein the larynx 63 lies in between the two coil windings 13, 23. The first and the second coil windings 13, 23 are spaced apart in distance D from each other. The distance D can vary according to varying physiologies of different patients and different treatments provided for the patient. A first winding axis C1 of the first coil winding 13 and a second winding axis C2 of the second coil winding 23 converge in direction towards the patient. Preferably, the first and the second winding axis C1 and C2 at least approximately intersect with the respective Phrenic nerve associated to the coil windings 13, 23. Preferably, the first and the second winding axis C1 and C2 lie in a common plane, which facilitates optimizing the electrical field exerted on the Phrenic nerves.

Advantageously, a respiration promoting apparatus comprising a bracket structure as discussed above is used for adjusting the positions and orientations of the coil units 10, 20. Like this, the coil windings 13, 23 can reliably and repeatedly positioned at the patient by taking advantage of support points provided by the coil units or their housings respectively. The term, "positioned at" as used herein can relate to being located at a patient's body by contacting it. For example, the three forward faces 11, 21, 31 of the stimulation device can be positioned at the body by lying on it. When being positioned at the body, the three forward faces 11, 21, 31 can form three support points and determine defined contact points on the body. Like this, the respiration promoting apparatus can be stably and precisely positioned with respect to the patient's Phrenic nerves. Further, by choosing a specific target configuration of the bracket structure 30 and specific contact points on the patient's body a defined location of the respiration promoting apparatus with respect to the patient is determined. The defined location is defined in that the first forward face 11, the second forward face 21 and the third forward face 31 provided at the bracket structure 30 are in contact with the patient at a position optimized for stimulating the Phrenic nerves 62.

In case that coil unit positioning without a bracket structure as discussed before is chosen, only two support points may be available corresponding to the first forward face of the first coil unit and the second forward face of the second coil unit. However, positions and orientations of the coil units may for example be adjusted manually. Alternatively, a suitable support structure may be provided configured to hold the first and the second coil units in a pre-set or adjustable position and orientation towards each other, which are suitable for generating the targeted electro-magnetic field of the respiration promoting apparatus.

The power supply 2 provides a current flow in the coil windings 13, 23 for example via a common current supply cable 1 and two current lines 42 running to each of the coil windings 13, 23. The power supply 2 advantageously is connected to or may include a control unit configured to coordinately provide a current flow through to the first and second coil windings 13, 23. Preferably, the control unit is configured such that current is provided simultaneously to the first and the second coil windings 13, 23 according to a circulation direction for each of the coil winding required to generate a target electro-magnetic field suitable to stimulate the two Phrenic nerves without impacting surrounding tissue.

In the example shown in FIG. 6, the winding directions of the two coil windings 13, 23 are identical. Therefore, the current direction is controlled by the control unit such that a flow direction of current $I_1$ in the first coil winding 13 is opposite to a flow direction of currents $I_2$ in the second coil winding. Each of the coil windings 13, 23 generates an electro-magnetic field 50 targeted towards their associated Phrenic nerve 62. The two electro-magnetic fields 50 decrease toward an area in between the two coil windings 13, 23, but any remaining overlap of the fields would result in mutual erasure of the fields and the resulting overall electro-magnetic field strength would be zero or near zero in this area. Consequently, for example the area around the larynx would not be affected by any electro-magnetic field generated by the respiration promoting apparatus. When using a respiration promoting apparatus having a bracket structure 30 as discussed above, this area also is kept clear of any components of the apparatus and is freely accessible for the treatment of the patient.

Further, in the shown embodiment the respiration promoting apparatus comprises a first biofeedback sensor 18 and a second biofeedback sensor 28. The biofeedback sensors 18 and 28 are coupled to the control unit and the power supply, respectively. When the coil units 10, 20 are positioned at the patient, the biofeedback sensors 18 and 28 are oriented such that they can receive feedback signals from the Phrenic nerves and the diaphragm, respectively, when current is provided through the first and second coil windings 13, 23. For example, the first biofeedback sensor is positioned at the patient such that it provides a first feedback signal about contractility of a first diaphragm hemisphere, and the second biofeedback sensor is positioned at the patient such that it provides a second feedback signal about contractility of a second diaphragm hemisphere. E.g., the biofeedback sensors can comprise electrodes to be positioned at or near the diaphragm of the patient. Thus, the first coil winding 10 and the second coil winding 20 can be controlled coordinately in accordance with the first feedback signal and the second feedback signal and the power supply can individually provide a current to each of the coil windings 13, 23. For example, a current strength or a pulse frequency can be changed in response to the feedback signals such that the first and second Phrenic nerves are stimulated, and a diaphragm of the patient is homogeneously activated.

Figure 7A:
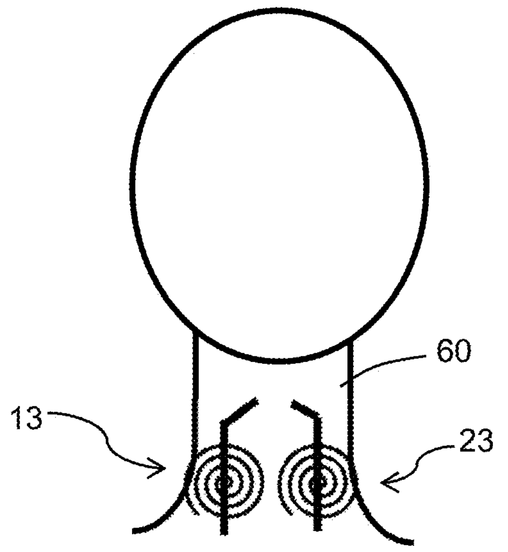
FIG. 7*a* shows a schematic view of a first coil winding and a second coil winding of the respiration promoting apparatus comprising a circular base shape.

FIG. 7*a* shows a schematic example of coil windings 13, 23 as presented in FIG. 6 and their placement at the neck 60 of the patient. As illustrated, the coil windings basically have circular shaped turns. They are essentially symmetric around their winding axis, although of course the turns are linked spiral-like to form a winding. Their base shape as defined by their turn with largest diameter can be described as being circular. According to their shape, such coil windings generate an electro-magnetic field that is symmetric around a centre of the field and turning the coil unit around its winding axis will not change the field distribution in the areas around the coil unit.

Figure 7B:
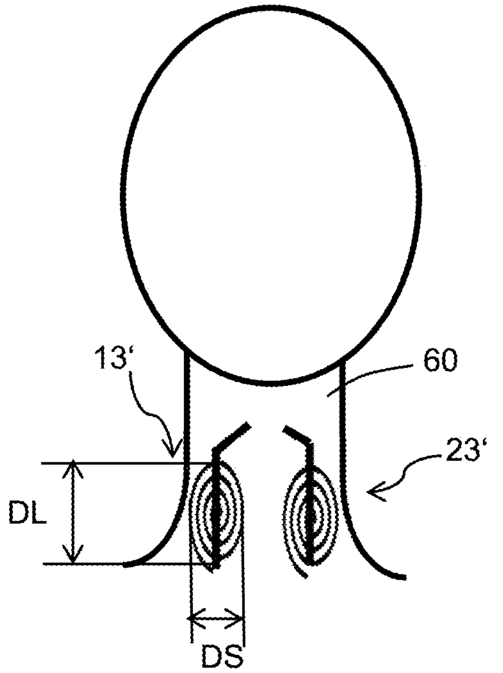
FIG. 7*b* shows a schematic view of a first coil winding and a second coil winding of the respiration promoting apparatus comprising an oval base shape.

In contrast to that, FIG. 7*b* shows a schematic example of coil windings 13', 23' comprising an oval shape and their orientation at the neck 60 of the patient. The turns of the coil windings 13', 23' are basically oval shaped. They are essentially symmetric to a plane including the winding axis. Their base shape as defined by their outermost turn is oval. Consequently, the outermost turn will have a large diameter DL in a first direction and a smaller diameter DS in a second direction perpendicular to the first direction.

The oval shape of the coil windings 13', 23' generates an oval shaped distribution of the electro-magnetic field produced by the coil units. A coil winding with an oval base shape produces an electro-magnetic field that is squeezed at opposing sides, when compared with the field produced by a coil winding of circular shape, if the large diameter DL of the oval shaped coil winding is equal to the diameter of the circular shaped coil winding. Consequently, the distribution of the electro-magnetic field of the oval shaped coil winding reaches less far in direction of the smaller diameter DS than in direction of the large diameter DL. Therefore, the electro-magnetic field resulting from the oval shaped coil winding 13', 23' can be more distant from critical tissue surrounding the Phrenic nerves while still reaching the Phrenic nerves.

Also, this allows positioning the coil units with oval shaped coil windings 13', 23' closer to such tissue than coil units with circular shaped coil winding without affecting such tissue. Advantageously, the two coil units 10, 20 are positioned such that their large diameters DL are parallel or nearly parallel to each other. For example, the first coil unit 10 having an oval shaped coil winding 13' and the second coil unit 20 having an oval shaped coil winding 23' can be placed closer to the sternocleidomastoid muscles, which may improve stimulation of the Phrenic nerves without impacting the muscles and may provide more space between the first and the second coil unit 10, 20.

As mentioned above, in a further embodiment the respiration promoting apparatus comprises three or more coil windings. FIGS. 8 to 12 illustrate the concept of such a respiration promoting apparatus comprising a third coil winding 70. As illustrated in these figures, the third coil winding 70 is formed from a conductive elongate component and is arranged in an area in between the first coil winding 13 and the second coil winding 23. FIG. 13 illustrates an embodiment of the respiration promoting apparatus comprising the third coil winding 70 and two additional coil windings 73*a* and 73*b*.

Figure 8:
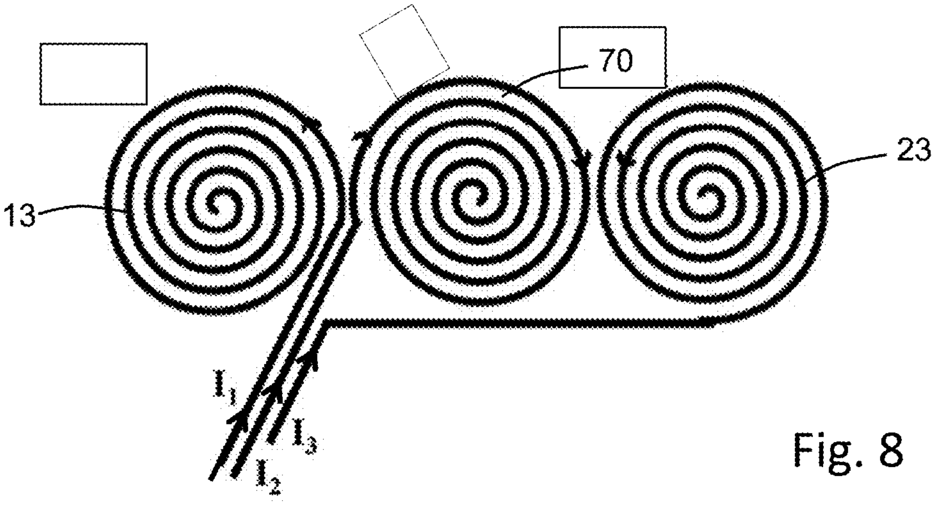
FIG. 8 shows a schematic view of an arrangement of a first coil winding, a second coil winding and a third coil winding of a respiration promoting apparatus according to the present invention.

In the example shown in FIG. 8, the first coil winding 13 comprises counter-clockwise windings, the second coil winding 23 comprises clockwise windings and the third coil winding 70 comprises counter-clockwise windings. Thus, the winding direction of the coil winding alternates between neighbouring coil windings. Each of the three coil windings 13, 23, 70 is individually provided with a current flow $I_1$, I2 and $I_3$ by the power supply 2. Strength and direction of the current flow is coordinated according to a required electro-magnetic field distribution for the treatment of the patient.

Particularly, the electro-magnetic field generated by the respiration promoting apparatus is configured to coordinatedly stimulate the two Phrenic nerves. The first coil winding 13 and the third coil winding 70 are arranged to provide a first electro-magnetic field peak area to stimulate the first Phrenic nerve of the patient. The second coil winding 13 and the third coil winding 70 are arranged to provide a second electro-magnetic field peak area to stimulate the second Phrenic nerve of the patient.

Figure 9:
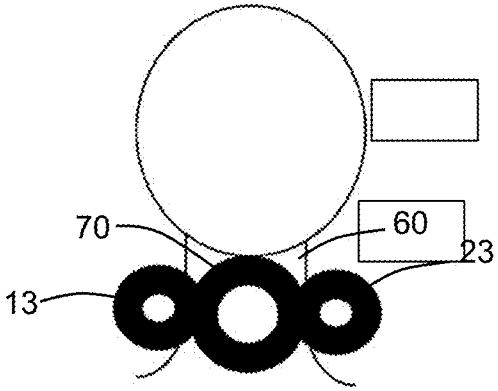
FIG. 9 shows a schematic view of applying a respiration promoting apparatus according to the present invention to a patient's neck.

FIG. 9 schematically illustrates the positioning of the respiration promoting apparatus comprising three coil winding at a patient's neck 60. The third coil winding 70 can be centred around the larynx of the patient. Also, the third coil winding 70 may have a central opening to provide access to the patient. The first coil winding 13 and the second coil winding 23 can be arranged at the sides of the right and left sternocleidomastoid muscles.

Figure 10:
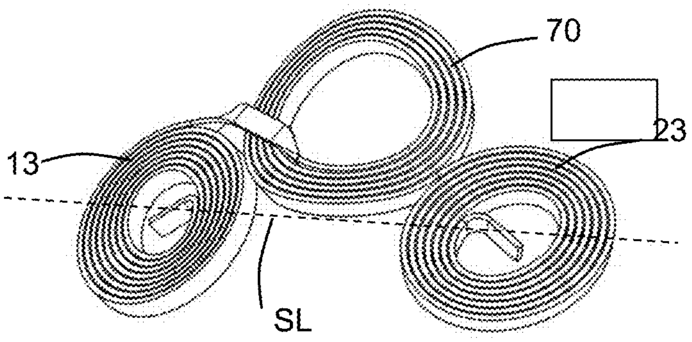
FIG. 10 shows a schematic view of a respiration promoting apparatus according to the present invention having a first coil winding and a second coil winding each comprising a flat shape, and a third coil winding comprising a bent shape.

FIG. 10 shows an embodiment of the respiration promoting apparatus having three coil winding, wherein the third coil winding 70 has an essentially bent shape while the first coil winding 13 and the second coil winding 23 are flat. Further, all three coil winding 13, 23, 70 are made from the same conductive elongate component. The elongate component starts in the centre of coil winding 13 and forms several turns spiraled outwardly to create the first coil winding 13. From the outermost turn of coil winding 13 the elongate component is bent over towards a central area of the third coil winding 70 and again forms several turns spiraled outwardly to create the third coil winding 70. The outermost turn of coil winding 70 continues to form an outermost turn for the second coil winding 23 and spirals inwardly to forms several turns to create the second coil winding 23. Thus, just one current flow I is required for simultaneously generating electro-magnetic fields with all three coil windings. Furthermore, in this embodiment the third coil winding 70 is offset with respect to a straight line SL connecting the centres of first coil winding 13 and second coil winding 23. The offset of the third coil winding 70 can be adapted to generate an optimized electro-magnetic field for stimulating the Phrenic nerves. Also, the location of the third coil winding 70 can be adjusted according to a patient's need.

Figure 11:
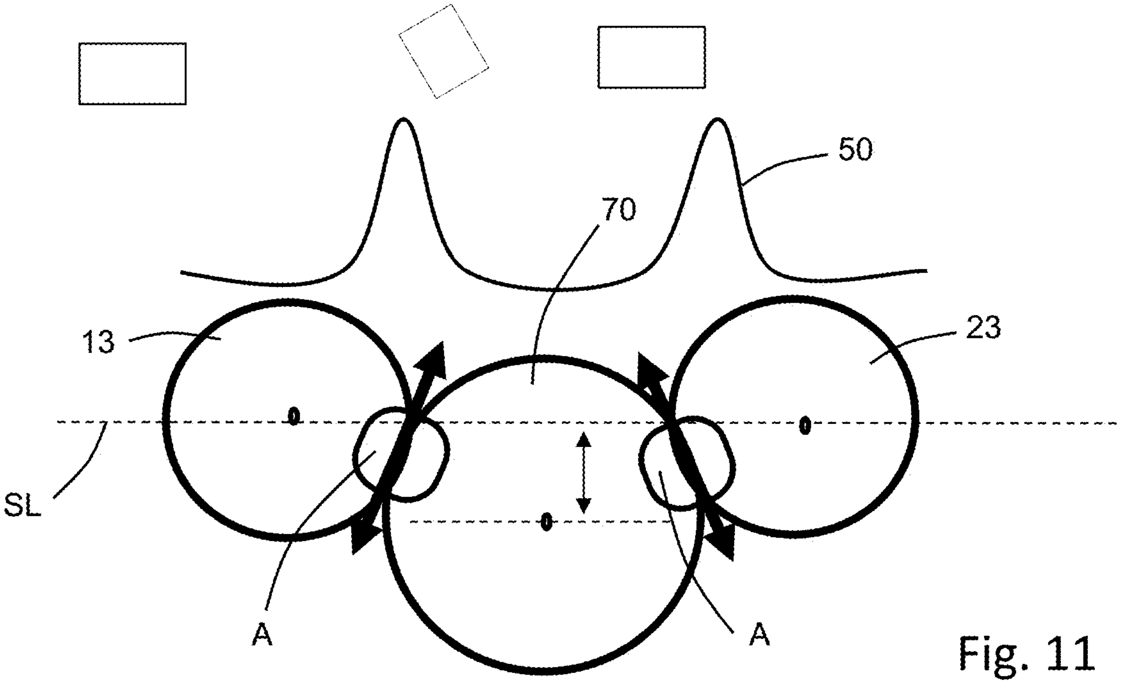
FIG. 11 shows a schematic view of an electro-magnetic field distribution of a respiration promoting apparatus comprising a coil winding arrangement as for example shown in FIG. 10.

FIG. 11 shows a schematic view of an electro-magnetic field distribution of a respiration promoting apparatus comprising a coil winding arrangement having a third coil winding 70 offset to the first coil winding 13 and the second coil winding 23 as for example shown in FIG. 10. However, such a field distribution could also be realized with non-flat coil windings as for example discussed in FIG. 6. The coil winding arrangement generates areas A of maximum electro-magnetic field strength. The arrows indicate a direction of the maximum electro-magnetic field. The resulting electro-magnetic field distribution 50 comprises to defined peaks positioned and oriented to coordinatedly stimulate the two Phrenic nerves for activating a diaphragm of the patient.

The third coil winding is used to strengthen the electro-magnetic field generated by the first and second coil windings. Preferably, the first and the second coil are located relative to the third coil winding such that the main electro-magnetic field direction is oriented in a direction that will depolarize the phrenic nerves. More preferably, the coil windings are located relative to each other such that the electro-magnetic field is not oriented parallel to the nerve.

Figure 12A:
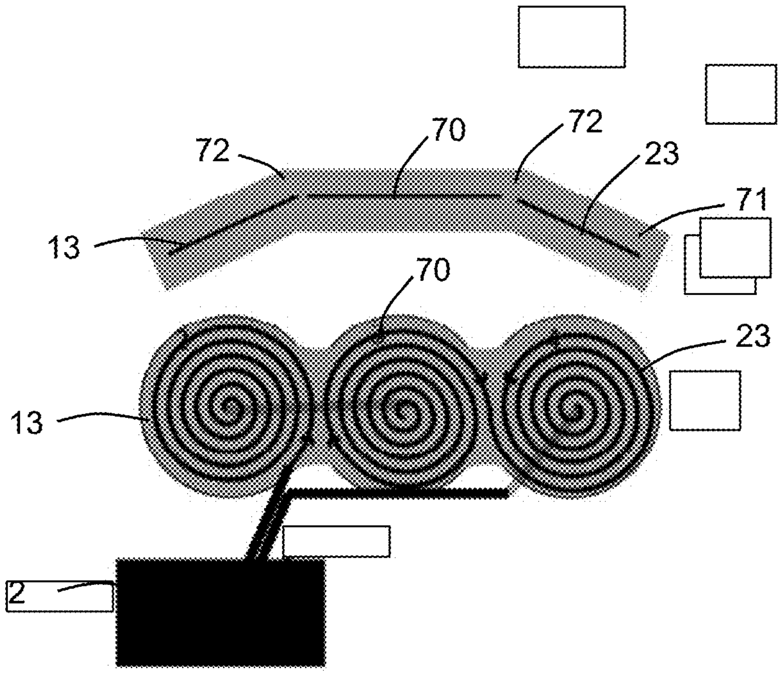
FIG. 12*a* shows a schematic view of a respiration promoting apparatus according to the present invention having a first coil winding, a second coil winding and a third coil winding, wherein the coil windings have a flat shape.
Figure 13:
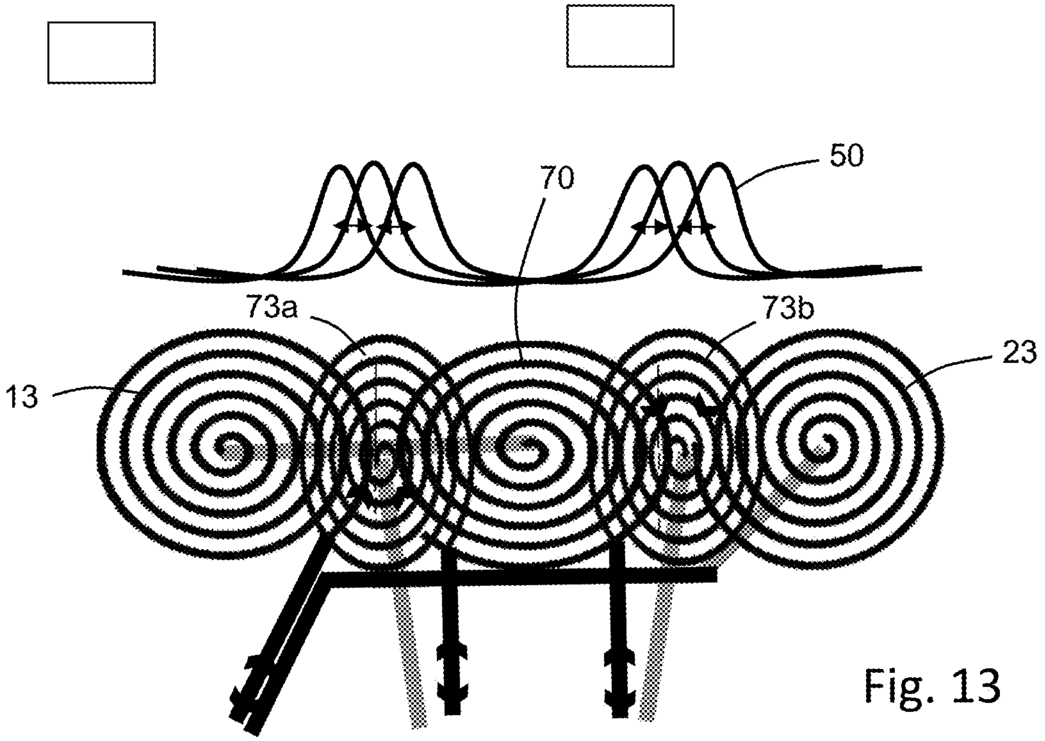
FIG. 13 shows a schematic view of an electro-magnetic field distribution of a respiration promoting apparatus comprising a coil winding arrangement as for example shown in FIG. 8 and additionally comprising a fourth coil winding and a fifth coil winding.

FIG. 12*a* shows a schematic view of a further example of a respiration promoting apparatus having a first coil winding 13, a second coil winding 23 and a third coil winding 70, wherein each of the coil windings has a flat shape. The coil windings 13, 23, 70 are formed by a single conductive elongate component as for example discussed for the example shown in FIG. 10. The coil windings 13, 23, 70 are all together encased in a common housing 71. A current flow I supplied to the first coil winding 13 by the power supply 2 and runs back to the power supply 2 from the second coil winding 23. The common housing 71 comprises flexible sections 72 configured for bending the common housing 71 as is illustrated in the upper part of FIG. 12*a*. The flexible section 72 allows for adjusting the orientation and position of the coil winding 13, 23, 70 around the patient's neck. Thus, the electro-magnetic field provided by the respiration promoting apparatus can be adapted to target the Phrenic nerves of the patient.

Figure 12B:
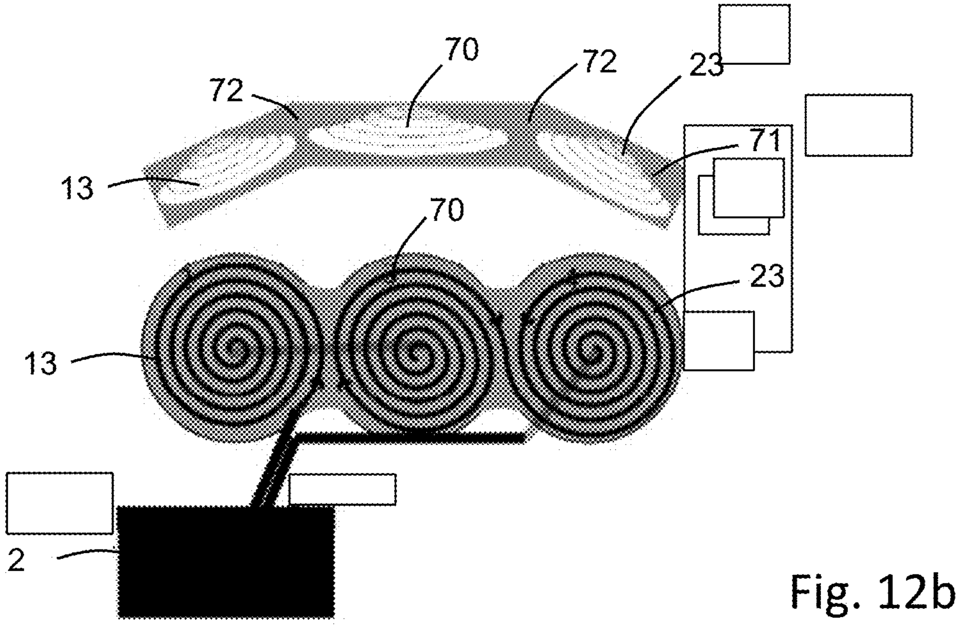
FIG. 12*b* shows a schematic view of a respiration promoting apparatus according to the present invention having a first coil winding, a second coil winding and a third coil winding, wherein the coil windings have a non-flat shape.

FIG. 12*b* shows a schematic view of still a further example of a respiration promoting apparatus having a first coil winding 13, a second coil winding 23 and a third coil winding 70 similar to the example FIG. 12*a*. However, in the example of FIG. 12*b* each of the coil windings has a non-flat convex shape as is illustrated in the upper part of FIG. 12*b*. The use of convex shaped coil winding has the above-mentioned benefits. The third coil winding 70 assists in targeting the electro-magnetic field resulting from the respiration promoting apparatus toward a target tissue like the Phrenic nerves and helps ta adjust the field to specific parameters of a patient.

FIG. 13 illustrates an embodiment of the respiration promoting apparatus comprising the third coil winding 70 as well as a fourth coil windings 73*a* and a fifth coil winding 73*b*. The fourth coil winding 73*a* overlaps with the first coil winding 13 and the third coil winding 70. The fifth coil winding 73*b* overlaps with the second coil winding 23 and the third coil winding 70. Each of the coil windings is connected to the power supply and individually provided with a current I. However, the coil windings of such a coil winding arrangement could also be connected to be provided with the same current flow. Advantageously, to positions of the fourth and fifth coil windings 73*a* and 73*b* are configured to adjust or shift the location of the two peaks in the electro-magnetic field distribution 50 generated by the over all coil winding arrangement. Preferably, the position and orientation of the fourth and fifth coil windings 73*a* and 73*b* can be adapted relative to the first coil winding 13, the second coil winding 23 and the third coil winding 70. Although all coil windings are shown in one line, the fourth and fifth coil windings 73*a* and 73*b* can be offset relative to the first and second coil winding 13 and 23 as discussed before for the third coil winding 70.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known structures and techniques have not been shown in detail in order not to obscure the invention. Thus, it will be understood that changes and modifications may be made by those of ordinary skill within the scope and spirit of the following claims.

In particular, the present invention covers further embodiments with any combination of features from different embodiments described herein. For example, it is possible to operate the invention in an embodiment wherein:

- the respiration promoting apparatus having a bracket structure is provided with non-flat coil windings, flat coil windings or a combination thereof,
- the respiration promoting apparatus having a bracket structure may have a third leg portion for mounting a third coil winding;
- the respiration promoting apparatus having a bracket structure may advantageously be used for stimulating two areas of other body tissue than the Phrenic nerves;
- the respiration promoting apparatus having a locking mechanism may advantageously be used for blocking the position of a common housing with flexible sections;
- the respiration promoting apparatus having non-flat coil windings may include additional coil windings in their respective coil unit; or
- the respiration promoting apparatus having non-flat coil windings may be used with other support structures for mounting the coil units than the bracket structure.

Further, embodiments comprising three coil windings described herein may disclose features of an inventive stimulation device, particularly a respiration promoting apparatus, that include innovative further developments without taking advantage of non-flat coil windings. For example, it is possible to operate the respiration promoting apparatus in a new and inventive manner by providing the first coil winding, the second coil winding and the third coil winding as flat coil windings, particularly as two-dimensional coil windings. Examples of such a respiration promoting apparatus are shown in FIGS. 10 and 12*a*. Therefore, the applicant reserves the right to file further patent applications based on the present application focusing on a stimulation device comprising a first coil winding configured to be positioned at a patient to stimulate a first nerve of the patient, a second coil winding configured to be positioned at the patient to stimulate a second nerve of the patient, and at least a third coil winding, which is arranged in an area in between the first coil winding and the second coil winding, wherein the coil windings are flat coil winding, non-fat coil windings or a combination thereof.

Further, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately", "basically" and the like in connection with an attribute or a value particularly also define exactly the attribute or exactly the value, respectively. Any reference signs in the claims should not be construed as limiting the scope.

REFERENCE SIGNS LIST

| | |
|---|---|
| 1 | current supply cable |
| 2 | power supply |
| 10 | first coil unit |
| 11 | first forward face |
| 12 | first leg portion |
| 13 | first coil winding |
| 15 | first through-hole |
| 16 | first housing |
| 17 | first backward face |
| 18 | first biofeedback sensor |
| 20 | second coil unit |
| 21 | second forward face |
| 22 | second leg portion |
| 23 | second coil winding |
| 25 | second through-hole |
| 26 | second housing |
| 27 | second backward face |
| 28 | second biofeedback sensor |
| 30 | bracket structure |
| 31 | third forward face |
| 32 | hinge portion |
| 33 | first pivoting coupler |
| 34 | second pivoting coupler |
| 35 | stem portion |
| 36 | branch portion |
| 37 | through-hole |
| 38 | locking button |
| 39 | bulge |
| 40 | clip mounting |
| 41 | extension plate |
| 42 | current line |
| 43 | fixation finger |
| 44 | connector |
| 50 | electro-magnetic field |
| 51 | peak ring |
| 52 | inner area |
| 60 | neck |
| 61 | sternocleidomastoid muscle |
| 62 | Phrenic nerve |
| 63 | larynx |
| 70 | third coil winding |
| 71 | common housing |
| 72 | flexible section |
| 73a | fourth coil winding |
| 73b | fifth coil winding |
| A | electro-magnetic field areas |
| A1 | first leg axis |
| A2 | second leg axis |
| A3 | first coupler axis |
| A4 | second coupler axis |
| C1 | first winding axis |
| C2 | second winding axis |
| D | distance first & second coil unit |

-continued

| | |
|---|---|
| DL | large diameter |
| DS | small diameter |
| H | hinge axis |
| S | free space |
| SL | straight line |

The invention claimed is:

1. A respiration promoting apparatus to coordinatedly stimulate a first Phrenic nerve and a second Phrenic nerve of a patient for activating a diaphragm of the patient, comprising:

a first coil unit configured to be positioned at a neck of the patient only on an area above the first Phrenic nerve of the patient to stimulate a first Phrenic nerve of the patient;

a second coil unit configured to be positioned at the neck of the patient only on an area above the second Phrenic nerve of the patient to stimulate a second Phrenic nerve of the patient; and a control unit configured to coordinatedly providing current to the first coil unit and to the second coil unit, wherein each of the first and second coil units is associated with only one of the first and second Phrenic nerves, wherein the first coil unit has a non-flat first coil winding formed from a conductive elongate component, wherein the second coil unit has a non-flat second coil winding formed from a conductive elongate component, wherein the control unit comprises a power supply coupled to the first coil winding of the first coil unit and to the second coil winding of the second coil unit, wherein the control unit is configured such that the power supply provides current through the first coil winding in a circulation direction and through the second coil winding in the same circulation direction, wherein the first coil unit has a first housing encasing the first coil winding and the second coil unit has a second housing encasing the second coil winding, and wherein the first and the second housing with the first and the second coil winding are configured to position and orient the first and second coil windings relative to the patient and relative to each other.

2. The respiration promoting apparatus of claim 1, wherein the first coil winding and the second coil winding are convex coil windings.

3. The respiration promoting apparatus of claim 2, wherein the convex coil windings have an essentially conical shape.

4. The respiration promoting apparatus of claim 2, wherein at least one of the convex coil windings has a cross section in an essentially spherical shape.

5. The respiration promoting apparatus of claim 2, wherein each of the first coil unit and the second coil unit has a forward face to be directed to a patient in use of the respiration promoting apparatus and a backward face opposite to the forward face, the forward face of the first coil unit is adjacent to a convex side of the first convex coil winding and the backward face of the first coil unit is adjacent to a concave side of the first convex coil winding, and the forward face of the second coil unit is adjacent to a convex side of the second convex coil winding and the backward face of the second coil unit is adjacent to a concave side of the second convex coil winding.

6. The respiration promoting apparatus of claim 1, wherein each of the first coil winding and the second coil winding has an oval base shape or an elliptical base shape.

7. The respiration promoting apparatus of claim 1, wherein the first coil winding has a first winding direction, the second coil winding has a second winding direction, and the first winding direction and the second winding direction are identical.

8. The respiration promoting apparatus of claim 1, wherein the control unit is configured to simultaneously provide current to the first coil unit and to the second coil unit.

9. The respiration promoting apparatus of claim 1, comprising a first biofeedback sensor coupled to the control unit and a second biofeedback sensor coupled to the control unit.

10. The respiration promoting apparatus of claim 9, wherein the control unit is configured to individually provide current to the first coil unit and to the second coil unit in accordance with signals received from the first biofeedback sensor and the second biofeedback sensor such that the diaphragm is uniformly activated.

11. The respiration promoting apparatus of claim 9, wherein the first biofeedback sensor is associated to the first coil unit and the second biofeedback sensor is associated to the second coil unit.

12. The respiration promoting apparatus of claim 1, comprising a third coil winding formed from a conductive elongate component, which is arranged in an area in between the first coil winding and the second coil winding.

13. The respiration promoting apparatus of claim 12, wherein the first coil winding and the third coil winding are arranged to provide a first electro-magnetic field peak to stimulate the first Phrenic nerve of the patient, and the second coil winding and the third coil winding are arranged to provide a second electro-magnetic field peak to stimulate the second Phrenic nerve of the patient.

14. The respiration promoting apparatus of claim 12, wherein at least the third coil winding has an essentially bent shape or kinked shape.

15. The respiration promoting apparatus of claim 12, wherein the first coil winding and the second coil winding comprise an oval base shape.

16. The respiration promoting apparatus of claim 12, wherein the third coil winding is offset with respect to a straight line connecting the first coil winding and the second coil winding.

17. A method for promoting respiration of a patient comprising:

positioning a non-flat first coil winding formed from a conductive elongate component at a neck of the patient such that a first Phrenic nerve of the patient is in an electro-magnetic field generatable by the first coil winding;

positioning a non-flat second coil winding formed from a conductive elongate component at the neck of the patient such that a second Phrenic nerve of the patient is in an electro-magnetic field generatable by the second coil winding, wherein the positioning of the non-flat first coil winding at the neck of the patient comprises positioning the non-flat first coil winding at the neck of the patient only on an area above the first Phrenic nerve of the patient to stimulate the first Phrenic nerve, and the positioning of the non-flat second coil winding at the neck of the patient comprises positioning the non-flat second coil winding at the neck of the patient only on an area above the second Phrenic nerve of the patient to stimulate the second Phrenic nerve such that each of the first and second coil windings is associated with only one of the first and second Phrenic nerves, wherein the non-flat first coil winding is encased by a first housing and the non-flat second coil winding is encased by a second housing, wherein the first and the second housing with the first and the second coil windings are configured to position and orient the first and second coil windings relative to the patient and relative to each other; and coordinatedly providing current through the first coil winding and the second coil winding such that the first and second Phrenic nerves are stimulated and a diaphragm of the patient is homogeneously activated, wherein the current through the first coil winding is provided in a circulation direction and the current through the second coil winding is provided in the same circulation direction.

18. The method of claim 17, wherein the first coil winding is oval shaped, wherein when the first coil winding is positioned at the patient, a large diameter of the first coil winding is arranged essentially parallel to the first Phrenic nerve of the patient, and the second coil winding is oval shaped, wherein when the second coil winding is positioned at the patient, a large diameter of the second coil winding is arranged essentially parallel to the second Phrenic nerve of the patient.

19. The method of claim 17, comprising:

positioning a first biofeedback sensor at the patient such that the first biofeedback sensor provides a first feedback signal about contractility of a first diaphragm hemisphere; and positioning a second biofeedback sensor at the patient such that the second biofeedback sensor provides a second feedback signal about contractility of a second diaphragm hemisphere, wherein current is coordinatedly provided through the first coil winding and the second coil winding in accordance with the first feedback signal and the second feedback signal.

20. The method of claim 17, comprising providing an electro-magnetic field by coordinatedly providing current through the first coil winding and the second coil winding such that a main electric field component direction is angled more than 20° and less than 160° relative to the Phrenic nerves.

* * * * *